United States Patent
Law et al.

(10) Patent No.: US 8,591,863 B2
(45) Date of Patent: Nov. 26, 2013

(54) COMPOSITIONS AGAINST CANCER ANTIGEN LIV-1 AND USES THEREOF

(75) Inventors: Debbie Law, Los Gatos, CA (US); Kurt Gish, Piedmont, CA (US)

(73) Assignee: Abbvie Biotherapeutics Inc., Redwood City, CA (US)

( * ) Notice: Subject to any disclaimer, the term of this patent is extended or adjusted under 35 U.S.C. 154(b) by 11 days.

(21) Appl. No.: 13/528,602

(22) Filed: Jun. 20, 2012

(65) Prior Publication Data

US 2012/0328513 A1 Dec. 27, 2012

Related U.S. Application Data

(63) Continuation of application No. 12/622,298, filed on Nov. 19, 2009, now abandoned, which is a continuation of application No. 11/962,593, filed on Dec. 21, 2007, now abandoned, which is a continuation of application No. 10/769,612, filed on Jan. 29, 2004, now abandoned.

(60) Provisional application No. 60/443,712, filed on Jan. 29, 2003.

(51) Int. Cl.
| | |
|---|---|
| A61K 51/00 | (2006.01) |
| A61K 39/00 | (2006.01) |
| C07K 16/00 | (2006.01) |
| C07K 17/00 | (2006.01) |
| C07K 17/14 | (2006.01) |
| C12P 21/08 | (2006.01) |

(52) U.S. Cl.
USPC ............... 424/1.49; 530/387.9; 530/387.3; 530/391.3; 530/391.1; 530/391.7; 424/178.1; 424/139.1; 424/133.1; 435/331; 435/328

(58) Field of Classification Search
None
See application file for complete search history.

(56) References Cited

U.S. PATENT DOCUMENTS

| | | | |
|---|---|---|---|
| 5,514,554 | A | 5/1996 | Bacus |
| 5,693,465 | A | 12/1997 | Manning et al. |
| 6,066,778 | A | 5/2000 | Ginsburg et al. |
| 6,762,020 | B1 | 7/2004 | Mack et al. |
| 6,884,869 | B2 | 4/2005 | Senter et al. |
| 7,091,186 | B2 | 8/2006 | Senter et al. |
| 7,098,308 | B2 | 8/2006 | Senter et al. |
| 7,141,549 | B2 | 11/2006 | Mezes et al. |
| 7,285,382 | B2 | 10/2007 | de Sauvage et al. |
| 7,288,248 | B2 * | 10/2007 | Bhaskar et al. ............ 424/130.1 |
| 7,498,298 | B2 | 3/2009 | Doronina et al. |

(Continued)

FOREIGN PATENT DOCUMENTS

| | | |
|---|---|---|
| WO | WO 98/18945 | 5/1998 |
| WO | WO 98/34118 | 8/1998 |

(Continued)

OTHER PUBLICATIONS

Bhaskar et al., "E-Selectin up-regulation allows for targeted drug delivery in prostate cancer," Cancer Research 63:6387-6394 (2003).

(Continued)

*Primary Examiner* — Cherie M Stanfield
(74) *Attorney, Agent, or Firm* — Seattle Genetics, Inc.

(57) ABSTRACT

Described herein are methods and compositions that can be used for diagnosis and treatment of cancer.

18 Claims, 9 Drawing Sheets

(56) References Cited

U.S. PATENT DOCUMENTS

| | | |
|---|---|---|
| 7,659,241 B2 | 2/2010 | Senter et al. |
| 7,691,566 B2 | 4/2010 | de Sauvage et al. |
| 7,705,120 B2 | 4/2010 | Lillie et al. |
| 7,982,015 B2 | 7/2011 | de Sauvage et al. |
| 2003/0215457 A1 | 11/2003 | Sauvage et al. |
| 2004/0096392 A1* | 5/2004 | Bhaskar et al. ............. 424/1.11 |
| 2004/0258616 A1 | 12/2004 | McLachlan et al. |
| 2005/0238649 A1 | 10/2005 | Doronina et al. |
| 2007/0264267 A1 | 11/2007 | de Sauvage et al. |
| 2008/0138345 A1 | 6/2008 | de Sauvage et al. |
| 2008/0175839 A1 | 7/2008 | Law et al. |

FOREIGN PATENT DOCUMENTS

| | | |
|---|---|---|
| WO | WO 99/23230 | 5/1999 |
| WO | WO 99/25877 | 5/1999 |
| WO | WO 99/33869 | 7/1999 |
| WO | WO 00/08210 | 2/2000 |
| WO | WO 01/55178 | 8/2001 |
| WO | WO 01/96372 | 12/2001 |
| WO | WO 03075855 A2 * | 9/2003 |
| WO | WO 2004/010957 | 2/2004 |
| WO | WO 2004/066933 | 8/2004 |
| WO | WO 2007/120787 | 10/2007 |

OTHER PUBLICATIONS

Børresen-Dale, A-L., "Genetic profiling of breast cancer: From molecular portraits to clinical utility," International Journal of Biological Markers 18:54-56 (2003).

DeRisi et al., "Use of a cDNA microarray to analyse gene expression patterns in human cancer," Nature Genetics 14:457-460 (1996).

Doronina et al., "Development of potent monoclonal antibody auristatin conjugates for cancer therapy," Nature Biotechnology 21:778-784 (2003).

Dressman et al., "Genes that co-cluster with estrogen receptor alpha in microarray analysis of breast biopsies," Pharmacogenomics Journal 1:135-41 (2001).

El-Tanani et al., "Interaction between estradiol and growth factors in the regulation of specific gene expression in MCF-7 human breast cancer cells," J. Steroid Biochem. Mol. Biol. 60:269-76 (1997).

El-Tanani et al., "Insulin/IGF-1 modulation of the expression of two estrogen-induced genes in MCF-7 cells," Mol. Cell Endocrinol. 121:29-35 (1996).

El-Tanani et al., "Interaction between estradiol and cAMP in the regulation of specific gene expression," Mol. Cell Endocrinol. 124:71-7 (1996).

EMBL Database, Accession No. U41060 (Dec. 23, 1995).

Francisco et al., "cAC10-vcMMAE, an anti-CD30-monomethyl auristatin E conjugate with potent and selective antitumor activity," Blood 102:1458-1465 (2003).

Khan et al., "Epression profiling in cancer using cDNA microarrays," Electrophoresis 20:223-229 (1999).

King et al., "Expression, purification and characterization of a mouse-human chimeric antibody and chimeric Fab' fragment," Biochem. J. 281:317-23 (1992).

Kobayashi et al., "Antitumor activity of TZT-1027, a novel dolastatin 10 derivative," Jpn J Cancer Res. 88:316-27 (1997).

Liefers et al., "Micrometastases and survival in stage II colorectal cancer," New England J. Med. 339:223-228 (1998).

Manning et al., "Oestrogen-regulated genes in breast cancer: Association of pLIV1 with lymph node involvement," Eur. J. Cancer 30:675-678 (1994).

Mohammad et al., "A new tubulin polymerization inhibitor, auristatin PE, induces tumor regression in a human Waldenstrom's macroglobulinemia xenograft model," Intl J. Oncology 154:367-372 (1999).

Payne et al., "Primary structure, functional expression, and chromosomal localization of the bumetanide-sensitive Na-K-Cl cotransporter in human colon," J. Biol. Chem. 270:17977-85 (1995).

Pettit et al., "Antineoplastic Agents 365. Dolastatin 10 SAR probes," Anti-Cancer Design 13:243-277 (1998).

Ross et al., "Prostate stem cell antigen as therapy target: Tissue expression and in vivo efficacy of an immunoconjugate," Cancer Research 61:2546-2553 (2002).

Taylor et al., "The LIV-1 gene, implicated in metastatic breast cancer, codes for a histidine-rich transmembrane protein," British Journal of Cancer 80(Suppl 2):24 (1999).

Taylor, K.M., "LIV-1 breast cancer protein belongs to new family of histidine-rich membrane proteins with potential to control intracellular Zn+2 Homeostasis," IUBMB Life 49:249-53 (2000).

Taylor et al., "The LZT proteins; the LIV-1 subfamily of zinc transporter," Biochimica et Biophysica Acta 1611:16-30 (2003).

Taylor et al., "Structure-function analysis of LIV-1, the breast cancer associated protein that belongs to a new subfamily of zinc transporters," Biochemical Journal 375:51-59 (2003).

Welford et al., "Detection of differentially expressed genes in primary tumor tissues using representational differences analysis coupled to microarray hybridization," Nucleic Acids Research 26:3059-3065 (1998).

Williams et al., "Analysis of differential expression in normal and neoplastic human breast epithelial cell lines," Electrophoresis 19:333-343 (1998).

Yamamoto et al., "Clinicial application of chimeric monoclonal antibody A7-NCS conjugate," Biotherapy 10:365-7 (1996), Abstract.

Yang et al., "Combining SSH and cDNA microarrays for rapid identification of differentially expressed genes," Nucleic Acids Research 27:1517-1523 (1999).

* cited by examiner

COMPOSITIONS AGAINST CANCER ANTIGEN LIV-1 AND USES THEREOF

CROSS REFERENCES TO RELATED APPLICATIONS

This application is a continuation of U.S. patent application Ser. No. 12/622,298, filed Nov. 19, 2009, which is a continuation of U.S. patent application Ser. No. 11/962,593, filed Dec. 21, 2007, now abandoned, which is a continuation of U.S. patent application Ser. No. 10/769,612, filed Jan. 29, 2004, now abandoned, which claims the benefit of U.S. Provisional Application No. 60/443,712, filed Jan. 29, 2003, all herein incorporated by reference.

REFERENCE TO A SEQUENCE LISTING

This application includes a sequence listing as a text file, named "0710-00115US_ST25.txt" created Aug. 26, 2009 and containing 25,269 bytes. The material contained in this text file is incorporated by reference in its entirety for all purposes.

FIELD OF THE INVENTION

The invention relates to the identification and generation of antibodies that specifically bind to LIV-1 proteins; and to the use of such antibodies and compositions comprising them, in the diagnosis, prognosis, and therapy of cancer.

BACKGROUND OF THE INVENTION

Zinc plays an essential role in cell growth, and is a cofactor of over 300 enzymes, including enzymes important in angiogenesis and cell remodeling. Vallee, B. L., Auld, D. S., Biochem. 29:5647-5659 (1990). Zinc associates with many macromolecules in cells, including molecular components that act to control growth, apoptosis, development and differentiation. Control of intracellular zinc levels, therefore, may be important in preventing the triggering of a variety of disease states, including cancer.

LIV-1 is a member of the LZT (LIV-1-ZIP Zinc Transporters) subfamily of zinc transporter proteins. Taylor, K. M. and Nicholson, R. I., Biochim. Biophys. Acta 1611:16-30 (2003). Computer analysis of the LIV-1 protein reveals a potential metalloprotease motif, fitting the consensus sequence for the catalytic zinc-binding site motif of the zincin metalloprotease.

The structure of LIV-1 implicates a role for the protein as a zinc-influx transporter protein. Experiments with recombinant LIV-1 localizes the protein to the plasma membrane, similarly concentrated in lamellipodiae as membrane-type metalloproteases. Taylor and Nicholson, supra. Computer analysis predicts six to eight transmembrane domains, a long extracellular N terminus, a short extracellular C terminus, as well as the consensus sequence for the catalytic zinc-binding site of metalloproteases. LIV-1 distribution studies indicates primary expression in breast, prostate, pituitary gland and brain tissue. Taylor and Nicholson, supra.

The LIV-1 protein has also been implicated in certain cancerous conditions, e.g. breast cancer and prostate cancer. The detection of LIV-1 is associated with estrogen receptor-positive breast cancer, McClelland, R. A., et al., Br. J. Cancer 77:1653-1656 (1998), and the metastatic spread of these cancers to the regional lymph nodes. Manning, D. A. et al., Eur. J. Cancer 30A:675-678 (1994). Antibodies useful for diagnosis, prognosis, and effective treatment of cancer, including metastatic cancer, would be desirable. Accordingly, provided herein are compositions and methods that can be used in diagnosis, prognosis, and therapy of certain cancers.

SUMMARY OF THE INVENTION

The present invention provides anti-LIV-1 antibodies that are useful for making conjugated antibodies for therapeutic purposes. For example, the anti-LIV-1 antibodies of the invention are useful as selective cytotoxic agents for LIV-1 expressing cells. In some embodiments, the antibodies of the present invention are therapeutically useful in persons diagnosed with cancer and other proliferative conditions, including benign proliferative conditions. In one aspect, the antibodies of the present invention can be used to treat proliferative conditions of the prostate or breast including, for example, prostate cancer or breast cancer.

The present invention provides antibodies that competitively inhibit binding of proteins encoded by vectors containing some or all of the sequence associated with LIV-1 (Hs.79136). In some embodiments the antibodies are further conjugated to an effector component. The effector component can be a label (e.g., a fluorescent label, an effector domain e.g. MicA) or can be a cytotoxic moiety (e.g., a radioisotope or a cytotoxic chemical). An exemplary cytotoxic chemical is auristatin-E. In other embodiments the antibodies can be used alone to inhibit tumor cell growth.

The antibodies of the invention can be whole antibodies or can be antibody fragments. In some embodiments the immunoglobulin is a humanized antibody. An exemplary antibody of the invention is defined by CDRs.

The invention further provides immunoassays using the immunoglobulins of the invention. These methods involve detecting a cancer cell in a biological sample from a patient by contacting the biological sample with an antibody of the invention. The antibody is typically conjugated to a label such as a fluorescent or other label.

The invention also provides double-stranded ribonucleic acids that bind to mRNA encoded by the LIV-1 nucleic acid of SEQ ID NO:1. The double-stranded ribonucleic acids may cover the length of the target mRNA, or may be short double-stranded ribonucleic acids complementary to the target mRNA, e.g. siRNA.

The invention also provides pharmaceutical compositions comprising a pharmaceutically acceptable excipient and the antibody or double stranded ribonucleic acid of the invention. In these embodiments, the antibody can be further conjugated to an effector component. The effector component can be a label (e.g., a fluorescent label) or can be a cytotoxic moiety (e.g., a radioisotope or a cytotoxic chemical). An exemplary cytotoxic chemical is auristatin-E. The antibodies in the pharmaceutical compositions can be whole antibodies or antibody fragments. In some embodiments the immunoglobulin is a humanized antibody.

The invention also provides methods of inhibiting proliferation of a prostate cancer-associated or breast cancer-associated cell. The method comprises contacting the cell with an antibody or double-stranded ribonucleic acid of the invention. In most embodiments, the cancer cell is in a patient, typically a human. The patient may be undergoing a therapeutic regimen to treat metastatic or benign prostate cancer or breast cancer or may be suspected of having prostate cancer or breast cancer.

DESCRIPTION OF THE TABLES AND FIGURES

Table 1 provides the cDNA (SEQ ID NO:1) and protein sequence for LIV-1 (SEQ ID NO:2).

Table 2 provides DNA and peptide sequences for the LIV-1 antibody, #1.7A4 (SEQ ID NOS:3-6).

Table 3 provides a partial list of the variety of medical conditions that LIV-1 may be implicated in.

Table 4 provides a list of cell lines that may be used to validate anti-LIV-1 compositions in ovarian and bladder systems.

Table 5 provides LIV-1 mutant (BCR4 M1) cDNA (5A) and protein sequences (5B). Mutated residues are underlined.

Table 6 provides a list of antibodies generated against the LIV-1 protein.

DETAILED DESCRIPTION OF THE INVENTION

Figure 1:
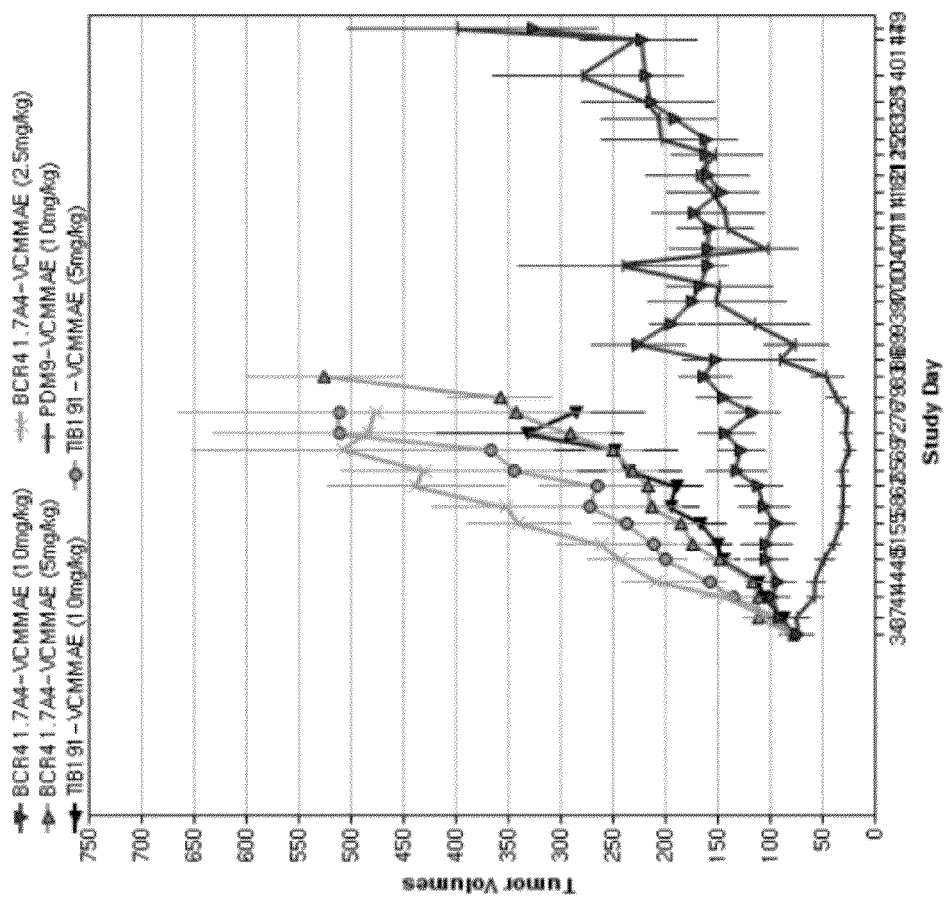
FIG. 1 shows a graph of the reduction in size of a prostate tumor in vivo after Auristatin-E-conjugated LIV-1 antibody treatment.

The present invention provides novel reagents and methods for treatment, diagnosis and prognosis for certain cancers using antibodies and double-stranded ribonucleic acids against LIV-1. In particular, the present invention provides anti-LIV-1 antibodies that are particularly useful as selective cytotoxic agents for LIV-1 expressing cells.

Epitope mapping of antibodies showing high affinity binding can be carried out through competitive binding analyses. Using this methodology, antibodies recognizing a number of individual epitopes can be identified. The antibodies are then assessed for LIV-1 dependent cell death in vitro. Using these methods antibodies that promote cell death can be identified.

Definitions

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., Immunology, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J. Immunol.:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., Nature Biotech. 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332: 323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "LIV-1 protein" or "LIV-1 polynucleotide" refers to nucleic acid and polypeptide polymorphic variants, alleles, mutants, and interspecies homologues that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of at least about 25, 50, 100, 200, 500, 1000, or more nucleotides, to a nucleotide sequence of SEQ ID NO:1; (2) bind to antibodies, e.g., polyclonal antibodies, raised against an immunogen comprising an amino acid sequence encoded by a nucleotide sequence of SEQ ID NO:1, and conservatively modified variants thereof; (3) specifically hybridize under stringent hybridization conditions to a nucleic acid sequence, or the complement thereof of SEQ ID NO:1 and conservatively modified variants thereof or (4) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino sequence identity, preferably over a region of at least about 25, 50, 100, 200, or more amino acids, to an amino acid sequence of SEQ ID NO:2. A polynucleotide or polypeptide sequence is typically from a mammal including, but not limited to, primate, e.g., human; rodent, e.g., rat, mouse, hamster; cow, pig, horse, sheep, or other mammal. A "LIV-1 polypeptide" and a "LIV-1 polynucleotide," include both naturally occurring or recombinant forms.

A "full length" LIV-1 protein or nucleic acid refers to a prostate cancer or breast cancer polypeptide or polynucleotide sequence, or a variant thereof, that contains all of the elements normally contained in one or more naturally occurring, wild type LIV-1 polynucleotide or polypeptide sequences. For example, a full length LIV-1 nucleic acid will typically comprise all of the exons that encode for the full length, naturally occurring protein. The "full length" may be prior to, or after, various stages of post-translation processing or splicing, including alternative splicing.

"Biological sample" as used herein is a sample of biological tissue or fluid that contains nucleic acids or polypeptides, e.g., of a LIV-1 protein, polynucleotide or transcript. Such samples include, but are not limited to, tissue isolated from primates, e.g., humans, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as E. coli, or eukaryotic cells such as yeast, insect, amphibian, or mammalian cells such as CHO, HeLa, and the like (see, e.g., the American Type Culture Collection catalog).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor & Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of (-sheet and (-helices. "Tertiary structure" refers to the complete three dimensional structure of a polypeptide monomer. "Quaternary structure" refers to the three dimensional structure formed, usually by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, $^{3}H$, $^{14}C$, $^{32}P$, $^{35}S$, or $^{125}I$. In some cases, particularly using antibodies against the proteins of the invention, the radioisotopes are used as toxic moieties, as described below. The labels may be incorporated into the LIV-1 nucleic acids, proteins and antibodies at any position. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982). The lifetime of radiolabeled peptides or radiolabeled antibody compositions may extended by the addition of substances that stablize the radiolabeled peptide or antibody and protect it from degradation. Any substance or combination of substances that stablize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin; activatable moieties, a chemotherapeutic agent; a chemoattractant, a lipase; an antibiotic; or a radioisotope emitting "hard" e.g., beta radiation.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, e.g., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background.

Specific binding to an antibody under such conditions requires an antibody that is selected for its specificity for a particular protein. For example, polyclonal antibodies raised to a particular protein, polymorphic variants, alleles, orthologs, and conservatively modified variants, or splice variants, or portions thereof, can be selected to obtain only those polyclonal antibodies that are specifically immunoreactive with LIV-1 and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

"Tumor cell" refers to precancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, Culture of Animal Cells a Manual of Basic Technique (3rd ed. 1994)).

Expression of LIV-1 Polypeptides from Nucleic Acids

Nucleic acids of the invention can be used to make a variety of expression vectors to express LIV-1 polypeptides which can then be used to raise antibodies of the invention, as described below. Expression vectors and recombinant DNA technology are well known to those of skill in the art and are used to express proteins. The expression vectors may be either self-replicating extrachromosomal vectors or vectors which integrate into a host genome. Generally, these expression vectors include transcriptional and translational regulatory nucleic acid operably linked to the nucleic acid encoding the LIV-1 protein. The term "control sequences" refers to DNA sequences used for the expression of an operably linked coding sequence in a particular host organism. Control sequences that are suitable for prokaryotes, e.g., include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is typically accomplished by ligation at convenient restriction sites. If such sites do not exist, synthetic oligonucleotide adaptors or linkers are used in accordance with conventional practice. Transcriptional and translational regulatory nucleic acid will generally be appropriate to the host cell used to express the LIV-1 protein. Numerous types of appropriate expression vectors, and suitable regulatory sequences are known in the art for a variety of host cells.

In general, transcriptional and translational regulatory sequences may include, but are not limited to, promoter sequences, ribosomal binding sites, transcriptional start and stop sequences, translational start and stop sequences, and enhancer or activator sequences. In a one embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, an expression vector may comprise additional elements. For example, the expression vector may have two replication systems, thus allowing it to be maintained in two organisms, e.g. in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art (e.g., Fernandez & Hoeffler, supra).

In addition, in another embodiment, the expression vector contains a selectable marker gene to allow the selection of transformed host cells. Selection genes are well known in the art and will vary with the host cell used.

The LIV-1 proteins of the present invention are produced by culturing a host cell transformed with an expression vector containing nucleic acid encoding a LIV-1 protein, under the appropriate conditions to induce or cause expression of the LIV-1 protein. Conditions appropriate for LIV-1 protein expression will vary with the choice of the expression vector and the host cell, and will be easily ascertained by one skilled in the art through routine experimentation or optimization. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Saccharomyces cerevisiae* and other yeasts, *E. coli, Bacillus subtilis*, Sf9 cells, C129 cells, 293 cells, Neurospora, BHK, CHO, COS, HeLa cells, HUVEC (human umbilical vein endothelial cells), THP1 cells (a macrophage cell line) and various other human cells and cell lines.

In one embodiment, the LIV-1 proteins are expressed in mammalian cells. Mammalian expression systems are also known in the art, and include retroviral and adenoviral systems. One expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter (see, e.g., Fernandez & Hoeffler, supra). Typically, transcription termination and polyadenylation sequences recognized by mammalian cells are regulatory regions located 3' to the translation stop codon and thus, together with the promoter elements, flank the coding sequence. Examples of transcription terminator and polyadenylyation signals include those derived from SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some embodiments, LIV-1 proteins are expressed in bacterial systems. Bacterial expression systems are well known in the art. Promoters from bacteriophage may also be used and are known in the art. In addition, synthetic promoters and hybrid promoters are also useful; e.g., the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the LIV-1 protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, LIV-1 polypeptides are produced in insect cells. Expression vectors for the transformation of insect cells, and in particular, baculovirus-based expression vectors, are well known in the art.

LIV-1 polypeptides can also be produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The LIV-1 polypeptides may also be made as a fusion protein, using techniques well known in the art. Thus, e.g., for the creation of monoclonal antibodies, if the desired epitope is small, the LIV-1 protein may be fused to a carrier protein to form an immunogen. Alternatively, the LIV-1 protein may be made as a fusion protein to increase expression, or for other reasons. For example, when the LIV-1 protein is a LIV-1 peptide, the nucleic acid encoding the peptide may be linked to other nucleic acid for expression purposes.

The LIV-1 polypeptides are typically purified or isolated after expression. LIV-1 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the LIV-1 protein may be purified using a standard anti-LIV-1 protein antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the LIV-1 protein. In some instances no purification will be necessary.

One of skill will recognize that the expressed protein need not have the wild-type LIV-1 sequence but may be derivative or variant as compared to the wild-type sequence. These variants typically fall into one or more of three classes: substitutional, insertional or deletional variants. These variants ordinarily are prepared by site specific mutagenesis of nucleotides in the DNA encoding the protein, using cassette or PCR mutagenesis or other techniques well known in the art, to produce DNA encoding the variant, and thereafter expressing the DNA in recombinant cell culture as outlined above. However, variant protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the LIV-1 protein amino acid sequence. The variants typically exhibit the same qualitative biological activity as the naturally occurring analogue, although variants can also be selected which have modified characteristics as will be more fully outlined below.

LIV-1 polypeptides of the present invention may also be modified in a way to form chimeric molecules comprising a LIV-1 polypeptide fused to another, heterologous polypeptide or amino acid sequence. In one embodiment, such a chimeric molecule comprises a fusion of the LIV-1 polypeptide with a tag polypeptide which provides an epitope to which an anti-tag antibody can selectively bind. The epitope tag is generally placed at the amino- or carboxyl-terminus of the LIV-1 polypeptide. The presence of such epitope-tagged forms of a LIV-1 polypeptide can be detected using an antibody against the tag polypeptide. Also, provision of the epitope tag enables the LIV-1 polypeptide to be readily purified by affinity purification using an anti-tag antibody or another type of affinity matrix that binds to the epitope tag. In an alternative embodiment, the chimeric molecule may comprise a fusion of a LIV-1 polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; HIS6 and metal chelation tags, the flu HA tag polypeptide and its antibody 12CA5 (Field et al., Mol. Cell. Biol. 8:2159-2165 (1988)); the c-myc tag and the 8F9, 3C7, 6E10, G4, B7 and 9E10 antibodies thereto (Evan et al., Molecular and Cellular Biology 5:3610-3616 (1985)); and the Herpes Simplex virus glycoprotein D (gD) tag and its antibody (Paborsky et al., Protein Engineering 3(6):547-553 (1990)). Other tag polypeptides include the FLAG-peptide (Hopp et al., BioTechnology 6:1204-1210 (1988)); the KT3 epitope peptide (Martin et al., Science 255:192-194 (1992)); tubulin epitope peptide (Skinner et al., J. Biol. Chem. 266:15163-15166 (1991)); and the T7 gene 10 protein peptide tag (Lutz-Freyermuth et al., Proc. Natl. Acad. Sci. USA 87:6393-6397 (1990)).

Antibodies to Cancer Proteins

Once the LIV-1 protein is produced, it is used to generate antibodies, e.g., for immunotherapy or immunodiagnosis. In some embodiments of the invention, the antibodies recognize the same epitope as the CDRs shown in Table 2. The ability of a particular antibody to recognize the same epitope as another antibody is typically determined by the ability of one antibody to competitively inhibit binding of the second antibody to the antigen. Any of a number of competitive binding assays can be used to measure competition between two antibodies to the same antigen. An exemplary assay is a BIACORE® (chemicals for use in biological assays) assay. Briefly in these assays, binding sites can be mapped in structural terms by testing the ability of interactants, e.g. different antibodies, to inhibit the binding of another. Injecting two consecutive antibody samples in sufficient concentration can identify pairs of competing antibodies for the same binding epitope. The antibody samples should have the potential to reach a significant saturation with each injection. The net binding of the second antibody injection is indicative for binding epitope analysis. Two response levels can be used to describe the boundaries of perfect competition versus non-competing binding due to distinct epitopes. The relative amount of binding response of the second antibody injection relative to the binding of identical and distinct binding epitopes determines the degree of epitope overlap.

Other conventional immunoassays known in the art can be used in the present invention. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moeity (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Methods of preparing polyclonal antibodies are known to the skilled artisan (e.g., Coligan, supra; and Harlow & Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate).

The immunization protocol may be selected by one skilled in the art without undue experimentation.

The antibodies may, alternatively, be monoclonal antibodies. Monoclonal antibodies may be prepared using hybridoma methods, such as those described by Kohler & Milstein, Nature 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of Table 1, a fragment thereof, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, pp. 59-103 (1986)). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some embodiments the antibodies to the LIV-1 proteins are chimeric or humanized antibodies. As noted above, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity.

Human antibodies can be produced using various techniques known in the art, including phage display libraries (Hoogenboom & Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

In some embodiments, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., Proc. Nat'l Acad. Sci. USA 8:5879 (1988); Bird et al., Science 242:4236 (1988); Glockshuber et al., Biochemistry 29:1362 (1990); U.S. Pat. No. 4,946,778, U.S. Pat. No. 5,132,405 and Stemmer et al., Biotechniques 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser, preferably 2, 3, 4, 5, or 6 such sequences. However, it is to be appreciated that some amino acid substitutions within the linker can be made. For example, a valine can be substituted for a glycine.

Methods of making scFv antibodies have been described. See, Huse et al., supra; Ward et al. supra; and Vaughan et al., supra. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that binds to LIV-1 coated plates or to cells expressing LIV-1 on their surface are expanded in *E. coli* and subjected to another round of panning. In this way, an enrichment of many fold occurs in 3 rounds of panning. Thus, even when enrichment in each round is low, multiple rounds of panning will lead to the isolation of rare phage and the genetic material contained within which encodes the scFv with the highest affinity or one which is better expressed on phage.

Regardless of the method of panning chosen, the physical link between genotype and phenotype provided by phage display makes it possible to test every member of a cDNA library for binding to antigen, even with large libraries of clones.

In one embodiment, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for the LIV-1 protein, the other one is for another cancer antigen. Alternatively, tetramer-type technology may create multivalent reagents.

In some embodiments, the antibodies to LIV-1 protein are capable of reducing or eliminating cells expressing LIV-1 (e.g., prostate cancer or breast cancer cells). Generally, at least a 25% decrease in activity, growth, size or the like is preferred, with at least about 50% being particularly preferred and about a 95-100% decrease being especially preferred.

By immunotherapy is meant treatment of prostate cancer or breast cancer with an antibody raised against LIV-1 proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen (e.g., LIV-1 or DNA encoding it) to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen, leading to an immune response.

In some embodiments, the antibody is conjugated to an effector moiety. The effector moiety can be any number of molecules, including labeling moieties such as radioactive labels or fluorescent labels, or can be a therapeutic moiety. In one aspect the therapeutic moiety is a small molecule that modulates the activity of the LIV-1 protein. In another aspect the therapeutic moiety modulates the activity of molecules associated with or in close proximity to the LIV-1 protein.

In other embodiments, the therapeutic moiety is a cytotoxic agent. In this method, targeting the cytotoxic agent to prostate cancer or breast cancer tissue or cells, results in a reduction in the number of afflicted cells, thereby reducing symptoms associated with prostate cancer or breast cancer. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin-E and the like. Cytotoxic agents also include radiochemicals made by conjugating radioisotopes to antibodies raised against prostate cancer or breast cancer proteins, or binding of a radionuclide to a chelating agent that has been covalently attached to the antibody. Targeting the therapeutic moiety to transmembrane prostate cancer or breast cancer proteins not only serves to increase the local concentration of therapeutic moiety in the prostate cancer or breast cancer afflicted area, but also serves to reduce deleterious side effects that may be associated with the therapeutic moiety.

Binding Affinity of Antibodies of the Invention

Binding affinity for a target antigen is typically measured or determined by standard antibody-antigen assays, such as BIACORE® competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 µM, preferably <100 nM, and most preferably <0.1 nM. Antibody molecules will typically have a $K_D$ in the lower ranges. $K_D$=[Ab-Ag]/[Ab] [Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds.

The antibodies of the invention specifically bind to LIV-1 proteins. By "specifically bind" herein is meant that the antibodies bind to the protein with a $K_D$ of at least about 0.1 mM, more usually at least about 1 µM, preferably at least about 0.1 µM or better, and most preferably, 0.01 µM or better.

Immunoassays

The antibodies of the invention can be used to detect LIV-1 or LIV-1 expressing cells using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37, Asai, ed. Academic Press, Inc. New York (1993); Basic and Clinical Immunology 7th Edition, Stites & Terr, eds. (1991).

Thus, the present invention provides methods of detecting cells that express LIV-1. In one method, a biopsy is performed on the subject and the collected tissue is tested in vitro. The tissue or cells from the tissue is then contacted, with an anti-LIV-1 antibody of the invention. Any immune complexes which result indicate the presence of a LIV-1 protein in the biopsied sample. To facilitate such detection, the antibody can be radiolabeled or coupled to an effector molecule which is a detectable label, such as a radiolabel. In another method, the cells can be detected in vivo using typical imaging systems. Then, the localization of the label is determined by any of the known methods for detecting the label. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

LIV-1 proteins can also be detected using standard immunoassay methods and the antibodies of the invention. Standard methods include, for example, radioimmunoassay, sandwich immunoassays (including ELISA), immunofluorescence assays, Western blot, affinity chromatography (affinity ligand bound to a solid phase), and in situ detection with labeled antibodies.

Suppression of Endogenous LIV-1 Gene Expression through the Use of RNAi

In many species, introduction of double-stranded RNA (dsRNA) which may alternatively be referred to herein as small interfering RNA (siRNA), induces potent and specific gene silencing, a phenomena called RNA interference or RNAi. siRNA, in particular, is capable of rendering genes nonfunctional in a sequence specific manner. This phenomenon has been extensively documented in the nematode *C. elegans* (Fire, A., et al, Nature, 391, 806-811, 1998), but is widespread in other organisms, ranging from trypanasomes to mouse. Recent experiments demonstrate the inhibition of gene expression in human somatic cells, including the embryonic kidney cell line 293 and the epithelial carcinoma cell line HeLa. Caplen, N. J., et al., P.N.A.S. 98:9742-9747 (2001). Depending on the organism being discussed, RNA interference has been referred to as "co-suppression", "post-transcriptional gene silencing", "sense suppression" and "quelling".

RNAi is attractive as a biotechnological tool because it provides a means for knocking out the activity of specific genes. It is particularly useful for knocking out gene expression in species that were not previously considered to be amenable to genetic analysis or manipulation.

In designing RNAi experiments there are several factors that need to be considered such as the nature of the dsRNA, the durability of the silencing effect, and the choice of delivery system. See Elbashir, S. M. et al., EMBO J 20:6877-6888 (2001).

To produce an RNAi effect, the dsRNA, or siRNA that is introduced into the organism should contain exonic sequences. Furthermore, the RNAi process is homology dependent, so the sequences must be carefully selected so as to maximize gene specificity, while minimizing the possibility of cross-interference between homologous, but not gene-specific sequences. Preferably the dsRNA exhibits greater than 90% or even 100% identity between the sequence of the dsRNA and the gene to be inhibited. Sequences less than about 80% identical to the target gene are substantially less effective. Thus, the greater homology between the dsRNA and the gene whose expression is to be inhibited, the less likely expression of unrelated genes will be affected.

In addition, the size of the dsRNA is important. dsRNA may be greater than 500 base pairs in length, however, smaller fragments can also produce an RNAi effect. In particular, fragments that are short enough to avoid activation of nonsequence specific dsRNA responses (e.g. interferon responses) are effective in silencing gene responses. See Elbashir, S. M., et al., Nature 411:494-498 (2001).

Introduction of dsRNA can be achieved by any method known in the art, including for example, microinjection, liposome transfection or electroporation. A variety of mechanisms by which dsRNA may inhibit gene expression have been proposed, but evidence in support of any specific mechanism is lacking (Fire, A., 1999; Caplen, N. J. et al., 2001).

Administration of Pharmaceutical and Vaccine Compositions

The antibodies, nucleic acids and polypeptides of the invention can be formulated in pharmaceutical compositions. Thus, the invention also provide methods and compositions for administering a therapeutically effective dose of an anti-LIV-1 antibody, a LIV-1 nucleic acid, or a LIV-1 polypeptide or protein. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). As is known in the art, adjustments for prostate cancer or breast cancer degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals. Thus the methods are applicable to both human therapy and veterinary applications. In one embodiment the patient is a mammal, preferably a primate. In other embodiments the patient is human.

The administration of the antibodies, nucleic acids and polypeptides of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly.

The pharmaceutical compositions of the present invention comprise an antibody, nucleic acid or polypeptide of the invention in a form suitable for administration to a patient. In one embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody, polypeptide or nucleic acid of the invention dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacologial Basis of Therapeutics (Hardman et al., eds., 1996)).

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art, e.g., Remington's Pharmaceutical Science and Goodman and Gillman, The Pharmacologial Basis of Therapeutics, supra.

The compositions containing antibodies, polypeptides or nucleic acids of the invention can be administered for therapeutic or prophylactic treatments. In therapeutic applications, compositions are administered to a patient suffering from a disease (e.g., a cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, administration route, efficiency, etc. Such prophylactic treatments may be used, e.g., in a mammal who has previously had cancer to prevent a recurrence of the cancer, or in a mammal who is suspected of having a significant likelihood of developing cancer.

It will be appreciated that the present prostate cancer or breast cancer protein-modulating compounds can be administered alone or in combination with additional prostate cancer or breast cancer modulating compounds or with other therapeutic agent, e.g., other anti-cancer agents or treatments.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, and LIV-1-specific antibodies of the invention. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example 1

Antibodies to the Target Protein LIV-1, Inhibit Prostate Tumor Cell Growth In Vivo The following example illustrates that LIV-1 antibodies are effective at reducing tumor volume in vivo. Animal studies were conducted using male SCID mice implanted with a prostate cancer cell line, LNCaP. The LNCaP cell line expresses the antigen recognized by LIV-1 antibodies. The protein and nucleic acid sequences of the anti-LIV-1 #1.7A4 antibodies which were effective in these experiments, are provided as SEQ ID NOS: 3, 4, 5, and 6 (Table 2). Tumors were allowed to grow until they reached a size of between 50-100 mm$^3$. At that time, animals were randomized into groups and subjected to treatment with either a.) an Auristatin-E-conjugated isotype control antibody, or b.) the Auristatin-E-conjugated LIV-1 antibody, 1.7A4.

Antibodies were administered at a dose of 10 mg/kg for a total of 10 doses given intra-peritoneally every four days. Tumor size was measured twice weekly for 38 days. At the conclusion of the study, only tumors in the group treated with Auristatin-E-conjugated LIV-1 antibodies showed regression. See FIG. 1.

Thus, these experiments showed that treatment with the Auristatin-E-conjugated LIV-1 antibody results in a significant tumor volume reduction. Therefore the Auristatin-E-conjugated LIV-1 antibodies function as anti-cancer therapeutics for the treatment of patients bearing LIV-1 expressing tumors.

Example 2

Antibodies to the Target Protein LIV-1, Inhibit Breast Tumor Cell Growth In Vivo The following example illustrates that LIV-1 antibodies are effective at reducing tumor volume in vivo. Animal studies were conducted using female SCID mice implanted with estrogen pellets. The fat pads of the mice were implanted with a breast cancer cell line, MCF7. The MCF7 cell line expresses the antigen recognized by LIV-1 antibodies. The protein and nucleic acid sequences of the anti-LIV-1 #1.7A4 antibodies which were one of the auristatin-E-conjugated-LIV-1 antibodies effective in these experiments, are provided as SEQ ID NOs: 3, 4, 5, and 6 (Table 2).

Tumors were allowed to grow until they reached a size of between 50-100 mm$^3$. At that time, animals were randomized into groups and subjected to treatment with either a.) vehicle, b.) an Auristatin-E-conjugated isotype control antibody, or c.) one of two Auristatin-E-conjugated LIV-1 antibodies, 1.7A4 or 1.1F10.

Figure 2:
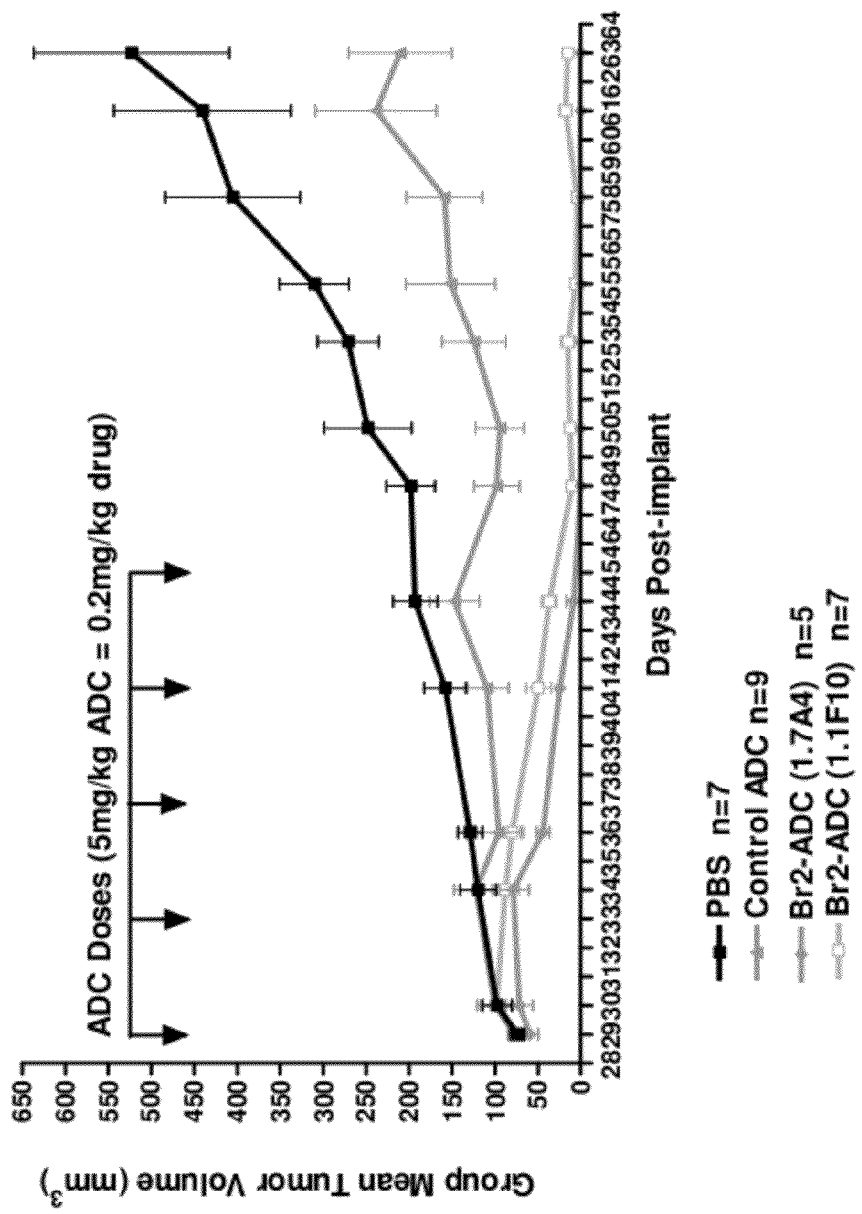
FIG. 2 shows a graph of the reduction in size of a breast cancer tumor in vivo after Auristatin-E-conjugated LIV-1 antibody treatment.

Antibodies were administered at a dose of 5 mg/kg for a total of 5 doses given intra-peritoneally every four days. Tumor size was measure twice weekly for 30 days. At the conclusion of the study, only tumors in the group treated with Auristatin-E-conjugated LIV-1 antibodies showed regression. See FIG. 2.

Thus, these experiments showed that treatment with the Auristatin-E-conjugated LIV-1 antibody results in a significant tumor volume reduction. Therefore the Auristatin-E-conjugated LIV-1 antibodies function as anti-cancer therapeutics for the treatment of patients bearing LIV-1 expressing tumors.

Example 3

Immunohistochemistry Analysis Using LIV-1 Antibodies

Tissue microarrays of primary breast cancer samples were obtained from Clinomics Biosciences, Inc. (Pittsfield, Mass.). Normal body tissues specimens were collected from samples harvested at the time of cadaveric organ donation from 6 individuals (3 males, 3 females obtained from Zoion, Hawthorne, N.Y.). IHC on formalin-fixed paraffin embedded tissues was performed using standard methods: heat induced antigen retrieval was performed in Dako Target Retrieval Solution for 15 minutes in a pressure cooker. Samples were then incubated with 1.1F10 anti-LIV-1 antibodies or control mouse IgG1 [TIB191, a mouse anti-trinitrophenol mAb (hybridoma clone 1B76.11)] for 30 minutes. Antibody binding was detected using biotinylated secondary antibody [Goat-anti-mouse IgG (3 mg/ml, 30 minutes; Jackson ImmunoResearch)], and developed using the Vectastain Elite ABC Kit (Vector Laboratories) and stable DAB (diaminobenzidine and H2O2; Research Genetics). Staining was performed using the DAKO Autostainer at room temperature.

Figure 3:
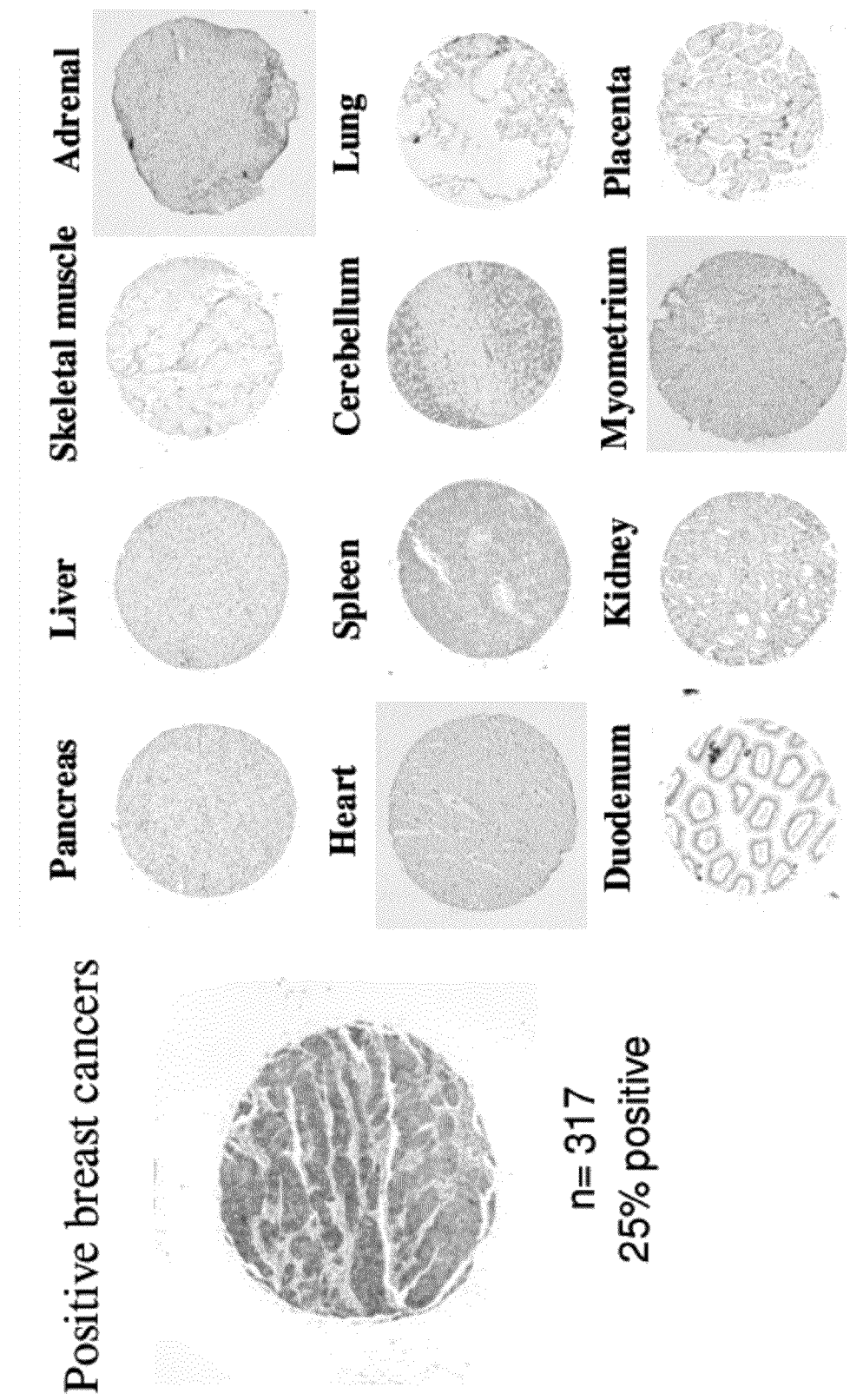
FIG. 3 shows fluorescence micrograph images of LIV-1 antibody stained tissue sections from breast cancer (left) and other normal tissues.

Analysis of primary breast cancer specimens showed that LIV-1-specific staining was restricted to the cytoplasm and membranes of the breast cancer epithelium, as compared to tissue specimens from pancreas, liver, skeletal muscle, adrenal gland, heart, spleen, cerebellum, lung, duodenum, kidney, myometrium and placenta, which showed no significant staining. See FIG. 3. The breast cancer cohort (n=133) displayed weak to strong staining in 27% of the cases, demonstrating that a large fraction of breast cancer patients exhibit expression of LIV-1. Analysis of a prostate cancer cohort (87 cases) demonstrated significant LIV-1 expression in 42% of the cases (data not shown). The staining in the prostate cancer specimens was also restricted to the glandular epithelium. These results demonstrate that LIV-1 protein is highly expressed in both breast and prostate cancer specimens. Therefore, LIV-1 is an attractive target for antibody-based therapy for both breast and prostate cancers.

Example 4

LIV-1 RNAi Clonogenic Assay

An RNAi Clonogenic assay was performed to determine the extent of LIV-1 siRNA targeted inhibition of carcinoma cell proliferation. MX-1 breast carcinoma cells were transfected with siRNAs using Lipofectamine 2000 (Invitrogen) according to the manufacturer's instructions except that cells were transfected in suspension as follows: MX-1 cells were diluted to 500 cells/ml. 0.5 ml was placed into each well of a 24 well plate containing 100 ul of a mixture of Lipofectamine 2000 (Invitrogen) and siRNAs in Minimal Essential Medium without phenol red (Invitrogen), with a final siRNA concentration of 10 nM. Each siRNA was assayed in four replicate wells. Cells were incubated at 37 C for 14-17 days, during which time the media was changed twice a week. The extent of cell proliferation was assessed by adding alamar blue to a final concentration of 12 ug/ml for 4-8 hours. Fluorescence was measured by excitation at 544 nm and emission at 590 nm.

siRNAs were purchased from Dharmacon as duplexes with 3' dTdT overhangs. siRNA sequences used are as follows:

```
H2R-1 (negative control) sense (SEQ ID NO: 7):
5'-CAGACACGGCCACGUGUGAdTdT-3'

H2R-1 antisense (SEQ ID NO: 8):
5'-UCACACGUGGCCGUGUCUGdTdT-3'

HKSP-1 (positive control) sense (SEQ ID NO: 9):
5'-GCUAGCGCCCAUUCAAUAGdTdT-3'

HKSP-1 antisense (SEQ ID NO: 10):
5'-CUAUUGAAUGGGCGCUAGCdTdT-3'
```

```
BCR4-53 sense (SEQ ID NO: 11):
5'-CAGCUUUUCUACCGCUAUGdTdT-3'

BCR4-53 antisense (SEQ ID NO: 12):
5'-CAUAGCGGUAGAAAAGCUGdTdT-3'
```

Figure 4:
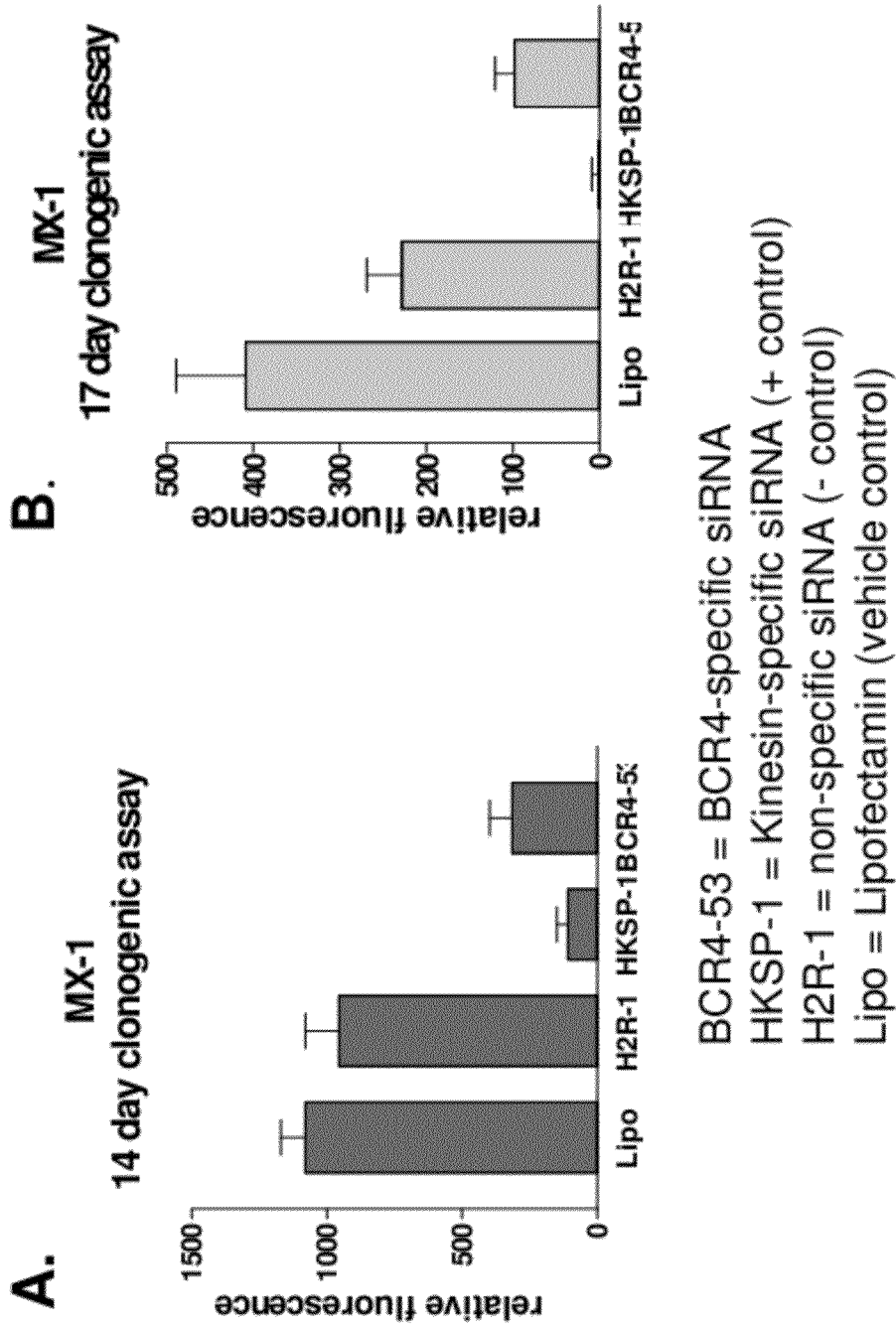
FIG. 4A shows a bar graph of the effect of a LIV-1 RNAi composition on MX-1 carcinoma cell growth in a clonogenic assay 14 days after addition of the LIV-1 siRNA.
FIG. 4B shows a bar graph of the effect of a LIV-1 RNAi composition has on MX-1 carcinoma cell growth in a clonogenic assay 17 days after addition of the LIV-1 siRNA.

The results indicate that downmodulation of LIV-1 by siRNA reduced carcinoma cell proliferation, as compared to controls. This indicates that LIV-1 expression is essential for proliferation in these carcinoma cells. As seen in FIGS. 4A & 4B, LIV-1 siRNA (BCR4-53; SEQ ID NOS:11 and 12) decreased cellular proliferation as compared to a non-specific siRNA control (H2R-1; SEQ ID NOS:7 and 8) in both 14- and 17-day cultures after addition of siRNA. The inhibition of cellular proliferation by LIV-1 siRNA was also comparable to a known inhibitor of carcinoma cell proliferation, HKSP-1 (SEQ ID NOS:9 and 10). This experiment, therefore, validates LIV-1 as a legitimate target for inhibiting cell proliferation.

Example 5

MMP Activity Assay

LIV-1 siRNA was also tested in a matrix metalloproteinase (MMP) activity assay. Cancer cells exhibit a variety of MMP activity, including MMP-2 and MMP-9 gelatinase activity. Increased MMP activity has been directly implicated in tumor cell invasion and angiogenesis because of their ability to degrade extracellular matrix components (see Olson, M. W. et al., J. Biol. Chem. 272:29975 (1997); MacDougall, J. R. et al., Cancer Metastasis Rev. 14:351 (1995); Cockett, M. I. et al, Biochem. Soc. Symp. 63:295 (1998)). MMP-2 and MMP-9 activity can be measured by determining the extent of gelatin degradation upon addition of carcinoma cells onto a gelatin matrix.

HCT-116 colorectal adenocarcinoma cells (obtained from NCI) were transfected with either BCR4-53 or H2R-1 siRNAs as described in the RNAi clonogenic assay with the following changes: 2.5 ml of cells at $2 \times 10^4$ cells/ml were plated into a single well of a 6 well plate containing 0.5 ml Lipofectamine-2000/siRNA mixture for a final siRNA concentration of 10 nM.

Cells were harvested approximately 72 hours after transfection by trypsinization, and counted using a hemacytometer. $1 \times 10^4$ cells in 1 ml media were plated onto fluorescent gelatin-coated glass coverslips in 24 well plates. Coverslips were prepared by acid washing and coated with 10 ul 0.5 mg/ml gelatin conjugated to Oregon Green (Molecular Probes). After drying, the gelatin was fixed with 0.5% glutaraldehyde for 15 minutes on ice, washed several times with H2O, and sterilized with 70% ethanol before the cells were plated on top. The plates were incubated at 37 C to allow the cells to attach and degrade the gelatin.

Approximately 24 hours after plating, the cells were fixed in Cytofix/Cytoperm (BD-Pharmingen). Total cellular LIV-1 protein levels were then assessed with anti-LIV-1 antibody (1.7A4) at 10 ug/ml, followed by F(ab')$_2$ goat anti-mouse IgG conjugated to Alexa Fluor 594 (Molecular Probes). Cell nuclei were also stained with 10 uM Hoechst 33342. The coverslips were mounted onto glass slides and subjected to fluorescence microscopy.

Figure 5:
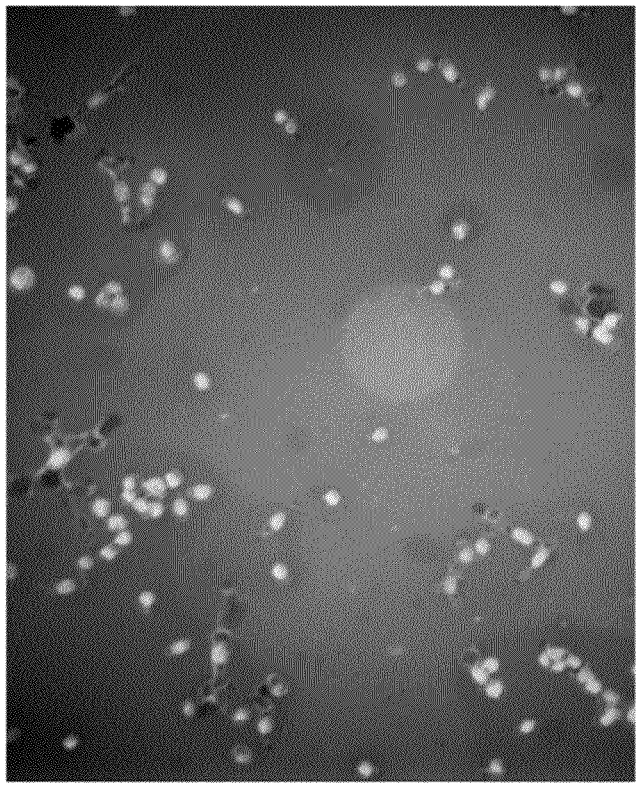
FIG. 5 shows a fluorescence microscope image of HCT116 cells transfected without (FIG. 5A) or with (FIG. 5B) a LIV-1 siRNA.
Figure 5:
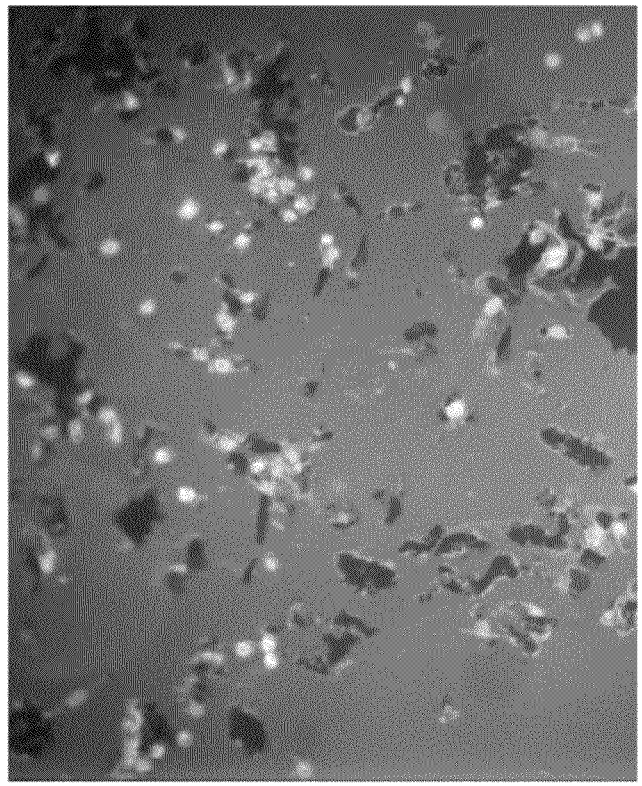

The results show (compare FIGS. 5A & 5B) that LIV-1 siRNA (SEQ ID NOS: 11 and 12) inhibited gelatin degradation by HCT-116 colorectal adenocarcinoma cells. This indicates, that LIV-1 is important in the upregulation of MMP-expression and/or activity in HCT-116 colorectal adenocarcinoma cells, and therefore validates LIV-1's role as a mediator in the extracellular invasion, and extracellular invasion and angiogenesis upregulation by carcinoma cells.

Example 6

Additional Antibodies to LIV-1

Monoclonal antibodies were raised against an N-terminus LIV-1 antigen and tested for binding on MX-1 cells by titration through FACS analysis. Hybridomas were derived from a fusion of NSO mouse myeloma cells and lymph nodes from mice immunized with purified protein containing the N-terminal 329 aa of LIV-1 fused to the human Fc domain. Hybridomas which expressed antibodies specific for LIV-1 were subcloned, implanted into mice, and antibodies were purified from ascites fluid.

Comparative binding of the various LIV-1 antibodies was assessed by flow cytometry. MX-1 breast carcinoma cells were incubated with a dilution series of LIV-1 and control antibody, followed by incubation with goat anti-mouse IgG conjugated to FITC (Caltag). Each dilution was done in triplicate.

Figure 6:
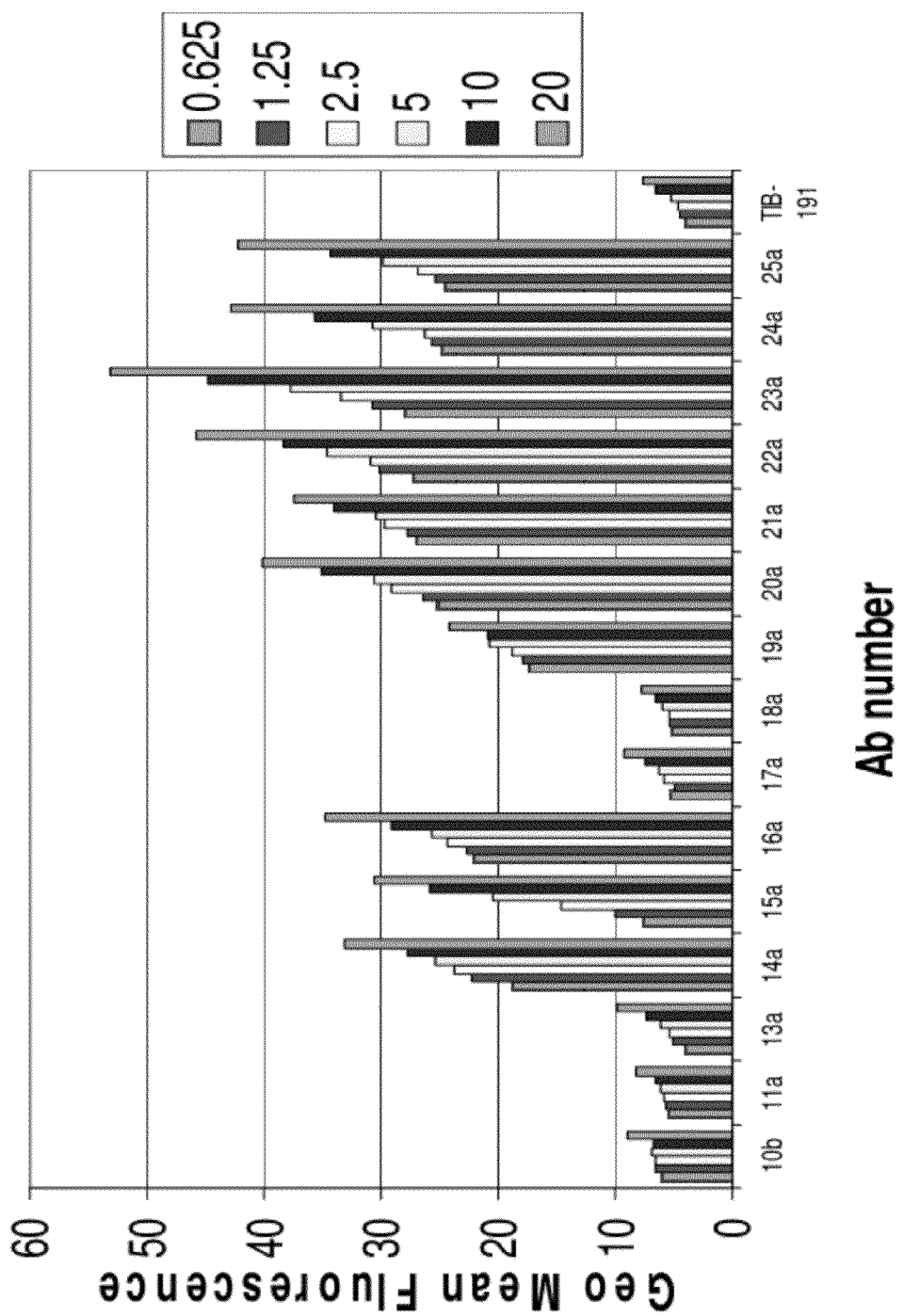
FIG. 6 shows a bar graph of the binding strength of various LIV-1 antibodies on LIV-1 expressing cells (MX-1 breast carcinoma cells).

The FACS results in FIG. 6 indicate that several LIV-1 antibodies show promising binding levels on MX-1 cells. In particular, LIV-1 antibodies 14 (ATCC accession number PTA-5705), 19 (ATCC accession number PTA-5706 and 23 (ATCC accession number PTA-5707).

Example 7

In Vitro Proliferation Assay with Toxin-Conjugated LIV-1 Antibodies

LIV-1 and control antibodies were conjugated to Auristatin-E containing a valine-citrulline peptide linker and purified by HPLC. Serial dilutions of two LIV-1 antibodies, 14a and 22a, were compared to a previously tested LIV-1 antibody (see Examples 1 and 2, supra), 1.7A4, and an IgG isotype control antibody for their ability to be internalized and kill LIV-1 expressing cells. 50 ul cells were plated into 96 well plates: CSOC 882-2 ovarian carcinoma cells at 650 cells/well, LNCaP prostate adenocarcinoma cells at 5000 cells/well, and MX-1 breast carcinoma cells at 650 cells/well. 24 hours after plating, 50 ul of the appropriate antibody dilution was added to triplicate wells and incubated for an additional 72 or 96 hours at 37 C. The extent of cell proliferation was assessed by adding alamar blue to a final concentration of 12 ug/ml and incubating at 37 C for 2 hours. Fluorescence was measured by excitation at 544 nm and emission at 590 nm. Fraction survival was calculated by normalizing cell survival of antibody-exposed cells to control cells growth in the absence of antibody.

Figure 7:
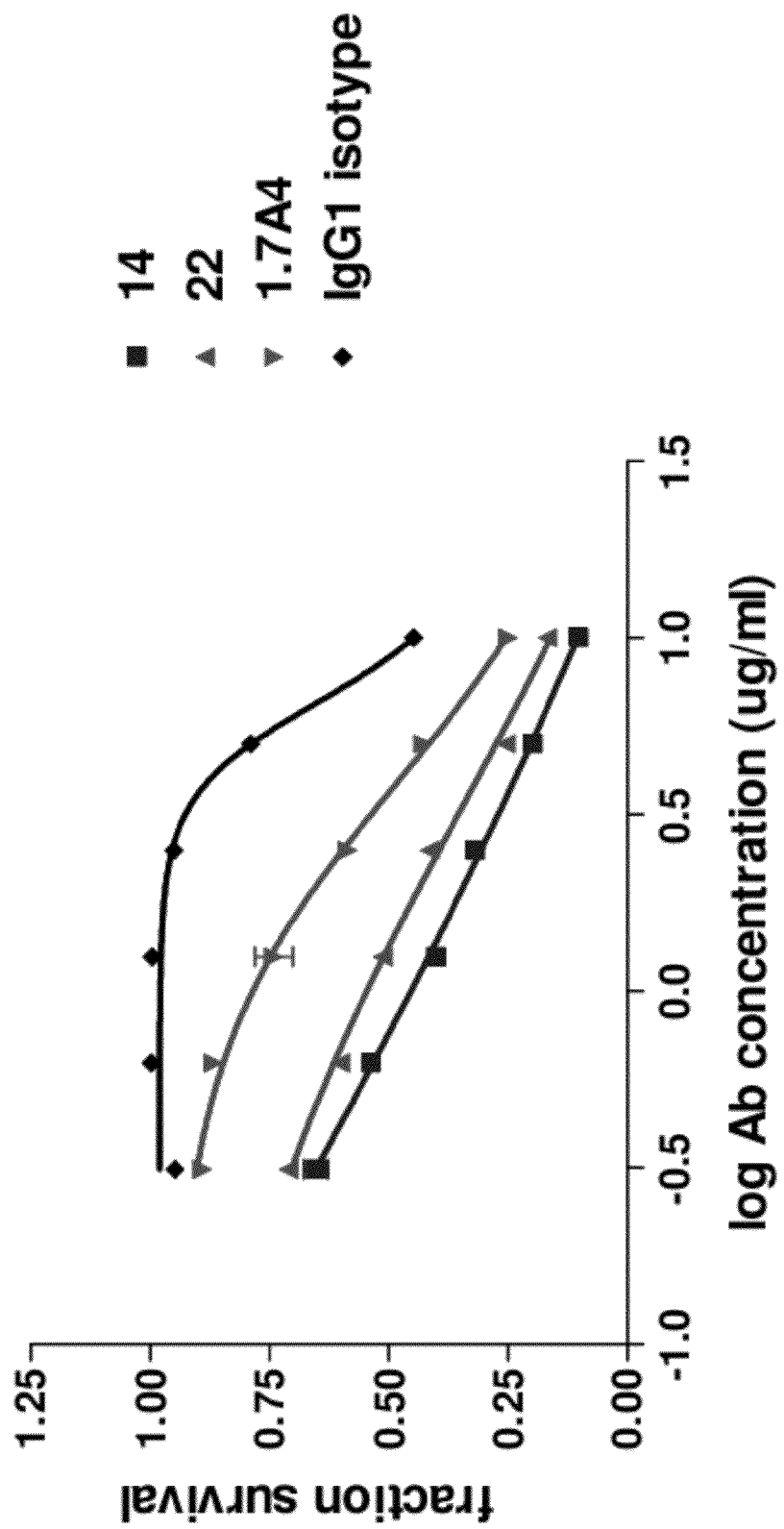
FIG. 7 shows the inhibition of several LIV-1 antibodies on epithelial ovarian carcinoma cell growth (CSOC), as compared to an isotype IgG1 control.
Figure 8:
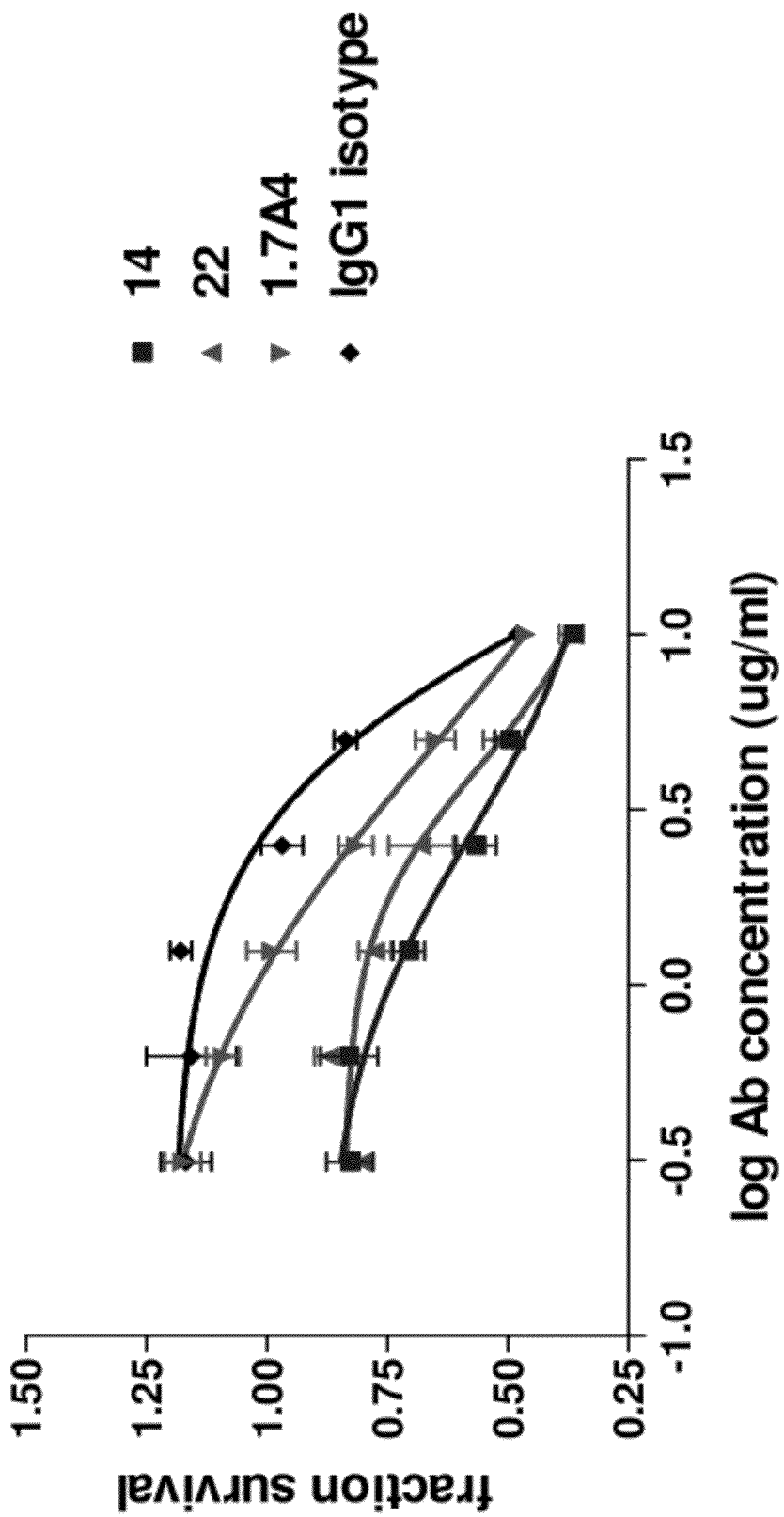
FIG. 8 shows the inhibition of several LIV-1 antibodies on mammary carcinoma cell growth (MX-1), as compared to an isotype IgG1 control.
Figure 9:
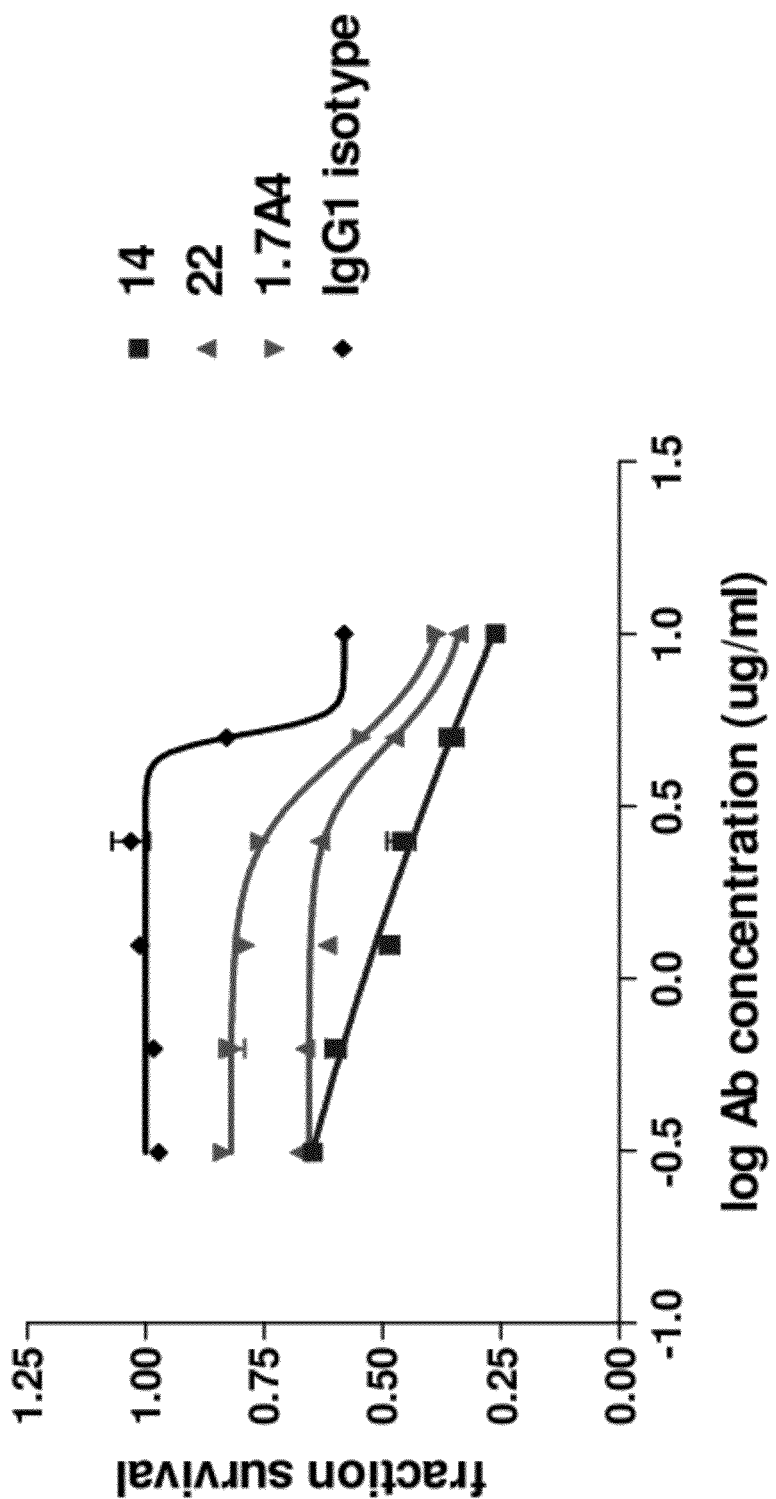
FIG. 9 shows the inhibition of several LIV-1 antibodies on prostate carcinoma cell growth (LNCaP), as compared to an isotype IgG1 control.

The results in FIGS. 7, 8 and 9 indicate that auristatin-E-conjugated 14a and 22a LIV-1 antibodies were more effective in in vitro growth assays using a variety of carcinoma cell types than the auristatin-E-conjugated 1.7a4 LIV-1 antibody. For CSOC (FIG. 7), MX-1 (FIG. 8) and LNCaP cells (FIG. 9), both 14a and 22a conjugated antibodies were more effective at tumor cell growth suppression than 1.7A4 LIV-1 antibody and a control IgG1 antibody. Therefore, the LIV-1 14a and 22a antibodies are useful in tumor cell growth suppression.

Example 8

Epitope Mapping of Anti-LIV-1 Antibodies Identifies Three Distinct Epitopes

Epitope mapping of BCR4 antibodies was done with flow cytometry using a competitive binding assay. MX-1 breast carcinoma cells were incubated with one of three FITC-conjugated antibodies in the presence or absence of a 10-fold molar excess of unconjugated (or naked) antibodies. In some experiments, the naked antibody was used at 5- or 20-fold molar excess with similar results. The ability of each naked antibody to compete with a FITC-conjugated antibody for binding was assessed. In all cases, naked antibodies either did not compete at all (−) or competed as well as the cognate naked antibody (+).

|  | FITC-conjugated Abs | | |
|---|---|---|---|
| Naked Abs | 14 | 19 | 21 |
| 13 | − | + | − |
| 14 | + | − | + |
| 15 | + | ND | + |
| 16 | + | ND | + |
| 19 | − | + | − |
| 20 | + | ND | + |
| 21 | + | ND | + |
| 22 | + | ND | + |
| 23 | + | ND | + |
| 24 | + | ND | + |
| 25 | + | ND | + |
| 1.7A4 | − | + | − |
| 1.1F10 | − | − | − |
| IGG1 ISOTYPE | − | − | − |

ND: not done

From this experiment we demonstrate that 9 of the antibodies bind the same or overlapping epitopes. These antibodies are 14, 15, 16, 20, 21, 22, 23, 24, and 25. The epitope bound by these antibodies is distinct from those of the previous antibodies we had generated and thus represents a novel epitope for potential therapeutic applications. The other two new antibodies, 13 and 19, represent an epitope binding group containing one of our previous antibodies, 1.7A4. A third epitope binding group, represented by 1.1F10 from our previous set of antibodies, was not represented in this new panel of antibodies.

Example 9

Mutant LIV-1 Protein

A mutant LIV-1 protein (BCR4 M1 cDNA (SEQ ID NO:13) and protein sequence (SEQ ID NO:14) provided in Table 5) was generated with a mutation in the putative MMP/Zn transporter domain. The goal to generating this mutant was to further characterize the biological activity of LIV-1.

This mutant was made using two rounds of PCR. Briefly two fragments were generated from the wild type gene via PCR using internal primers carrying the desired mutations.

The 5' end was generated using primers

```
                                        (SEQ ID NO: 15)
1 (CTTTAATTAACACCGCCACCATGGCGAGGAAGTTATCTGTAATC)
and
                                        (SEQ ID NO: 16)
2 (TAATGCAGCAGGCAACGCAGCACAGAACACAGCAACAGAAG).
```

The 3' end was generated using primers

```
                                        (SEQ ID NO: 17)
3 (TGCTGCGTTGCCTGCTGCATTAGGTGACTTTGCTGTTC)
and
                                        (SEQ ID NO: 18)
4 (GTCTCGAGGAAATTTATACGAAAC).
```

Since primers 2 and 3 contain overlapping sequences the two gene fragments were gel purified and used as overlapping templates in a second round of PCR using primers 1 and 4. The product of this second round PCR were cloned into pCR4 top( ) blunt and selected clones were sequenced. The desired mutant was selected and subcloned into the NEF39 expression vector and transfected into 3T12 cells. Overexpressing cells were isolated using a CD4-based screening procedure.

The isolated clones expressed significantly higher levels of mutant LIV-1 protein compared to clones isolated from experiments in which wild-type LIV-1 protein were transfected into 3T12 cells (data not shown). This result suggests that a functional activity, possibly MMP and/or Zn transporter activity, limits the amount of LIV-1 protein that can be expressed in a cell. It is known that expressing high levels of certain oncogenes in cells is difficult, because these oncogenes activate signaling pathways that under normal tissue culture conditions lead to cell death. It is possible that LIV-1 activity has a similar effect in cells and that mutational inactivation abrogates this effect, allowing for higher overexpression. This result suggests a functional role for LIV-1 in regulating cell proliferation and/or cell survival.

Example 10

Use of LIV-1 Antibodies to Delay the Onset of Androgen-Independence of Prostate Cancer and/or to Treat Androgen-Independent Disease Prostate cancer is a hormone regulated disease that affects men in the later years of life. Untreated prostate cancer metastasizes to lymph nodes and bone in advanced cases. In such cases current treatment consists of antagonizing the androgenic growth-stimulus that feeds the tumor by chemical or surgical hormone-ablation therapy (Galbraith and Duchesne. (1997) Eur. J. Cancer 33:545-554). An unfortunate consequence of anti-androgen treatment is the development of androgen-independent cancer. Androgen regulated genes such as the gene encoding prostate-specific antigen (PSA) are turned off with hormone-ablation therapy, but reappear when the tumor becomes androgen-independent (Akakura et al. (1993) Cancer 71:2782-2790). There are no viable treatment regimens for androgen-independent prostate cancer.

To study the progression of androgen-dependent prostate cancer to androgen-independent prostate cancer, the human CWR22 prostate cancer xenograft model was propagated in nude mice (see Pretlow, et al. (1993) J. Natl. Cancer Inst. 85:394-398). The CWR22 xenograft is androgen-dependent when grown in male nude mice. Androgen-independent sublines can be derived by first establishing androgen-dependent tumors in male mice. The mice are then castrated to remove the primary source of growth stimulus (androgen), resulting in tumor regression. Within 3-4 months, molecular events prompt the tumors to relapse and start growing as androgen-independent tumors. See, e.g., Nagabhushan, et al. (1996) Cancer Res. 56:3042-3046; Amler, et al. (2000) Cancer Res. 60:6134-6141; and Bubendorf, et al. (1999) J. Natl. Cancer Inst. 91:1758-1764.

We have previously monitored the gene expression changes that occur during the transition from androgen-dependence to androgen-independence using the CWR22 xenograft model (see WO02098358). Tumors were grown subcutaneously in male nude mice. Tumors were harvested at different times after castration. The time points ranged from 0 to 125 days post-castration. Castration resulted in tumor regression. At day 120 and thereafter, the tumors relapsed and started growing in the absence of androgen.

Gene expression profiling of the harvested tumors was accomplished using the Eos Hu03 oligonucleotide microarray (Affymetrix Eos Hu03) (Henshall et al. (2003) Cancer Res. 63:4196-4203). Our results identified several hundred genes that exhibited significant gene expression changes associated with androgen ablation therapy. Some genes were associated with the androgen-dependent growth phase of the CWR22 tumors (pre-castration and 1-5 days post-castration), some genes were associated with the androgen-withdrawal phase (10-82 days post castration, characterized by tumor regression and/or tumor growth stasis), and some genes were associated with the androgen-independent growth of CWR22 (greater than 120 days post castration). See WO02098358. From these results, we determined that the gene encoding LIV-1 is not androgen-regulated and exhibited high expression levels in androgen-dependent tumors and in all tumors undergoing androgen-withdrawal experiment, including tumors that grew in an androgen-independent manner (data not shown).

Castrated CWR22 xenograft nude male mice would be used as a model system for prevention of androgen-independent prostate cancer growth. CWR22 tumor bearing mice would be treated, post androgen-ablation therapy (castration), with anti-LIV-1 antibody conjugated with Auristatin-E. Post-castration treatment with anti-LIV-1 conjugated with Auristatin-E during the androgen-withdrawal phase (10-82 days post castration) should result in a delay in the onset of androgen-independent CWR22 tumor growth.

To accomplish this, CWR22 tumors would be grown in male immunodeficient mice for 2-3 weeks. The mice would then be castrated to induce tumor regression and entry into the androgen-withdrawal phase. Twenty days post-castration the tumors would be treated with anti-LIV-1 conjugated with Auristatin-E as described in Examples 1 and 2. A significant effect of anti-LIV-1-Auristatin-E would manifest itself in a delay in the onset of androgen-independence (e.g., 5 months or more post castration). This would suggest that androgen-ablation therapy patients with advanced stage prostate cancer would greatly benefit from treatment with humanized anti-LIV-1 drug conjugates.

A non-significant effect of anti-LIV-1 ADC treatment would be due to several potential factors: (a) CWR22 xenograft tumors may be resistant to Auristatin E; (b) the tumor cells may not efficiently internalize anti-LIV-1 ADC during the androgen-withdrawal phase; or (c) LIV-1 protein expression may be significantly decreased during the androgen-withdrawal phase. Modifications in treatment are available to address these issues.

As a model system for treating established androgen-independent prostate cancer, CWR22 tumor bearing mice would be treated at the time of onset of androgen-independence with anti-LIV-1 drug conjugate. The objective would be to show that post-castration treatment with anti-LIV-1 drug conjugates during the emergence of androgen-independence (>120 days post castration) would result in regression of androgen-independent CWR22 tumors.

CWR22 tumors would be grown in male immunodeficient mice for 2-3 weeks. The mice would be then castrated to induce tumor regression and entry into the androgen-withdrawal phase. Ten days after the tumors start growing in an androgen-independent manner, the tumors would be treated with anti-LIV-1 conjugated with Auristatin-E as described in Examples 1 and 2. A significant effect of anti-LIV-1-Auristatin-E would manifest itself in regression of androgen-independent tumors. This would suggest that patients that were treated with androgen-ablation therapy and that suffered relapse in the form of androgen-independent tumor growth and metastasis would greatly benefit from treatment with humanized anti-LIV-1 drug conjugate.

ATCC DEPOSIT

Under the terms of the Budapest Treaty on the International Recognition of the Deposit of Microorganisms for the Purpose of Patent Procedure, the hybridomas that produce antibodies BR2-14a, BR2-19a, BR2-22a, and BR2-23a (aka antibodies 14, 19, 22, and 23, respectively) were deposited with the American Type Culture Collection (ATCC). The deposit of the hybridomas that produce antibodies BR2-14a, BR2-19a, and BR2-23a, were deposited on Dec. 19, 2003 and accorded accession numbers PTA-5705, PTA-5706, and PTA-5707, respectively. The hybridoma that produces antibody BR2-22a was deposited on Nov. 11, 2010 and accorded accession number PTA-11478. The ATCC is located at 10801 University Boulevard, Manassas, Va. 20110-2209, USA.

TABLE 1

DNA AND PROTEIN SEQUENCES OF LIV-1
(GENBANK ACCESSION NM_012319)

SEQ ID NO: 1
LIV-1 DNA SEQUENCE

CTCGTGCCGA ATTCGGCACG AGACCGCGTG TTCGCGCCTG GTAGAGATTT CTCGAAGACA

CCAGTGGGCC CGTGTGGAAC CAAACCTGCG CGCGTGGCCG GGCCGTGGGA CAACGAGGCC

GCGGAGACGA AGGCGCAATG GCGAGGAAGT TATCTGTAAT CTTGATCCTG ACCTTTGCCC

TCTCTGTCAC AAATCCCCTT CATGAACTAA AAGCAGCTGC TTTCCCCCAG ACCACTGAGA

AAATTAGTCC GAATTGGGAA TCTGGCATTA ATGTTGACTT GGCAATTTCC ACACGGCAAT

ATCATCTACA ACAGCTTTTC TACCGCTATG GAGAAAATAA TTCTTTGTCA GTTGAAGGGT

TCAGAAAATT ACTTCAAAAT ATAGGCATAG ATAAGATTAA AAGAATCCAT ATACACCATG

ACCACGACCA TCACTCAGAC CACGAGCATC ACTCAGACCA TGAGCGTCAC TCAGACCATG

AGCATCACTC AGACCACGAG CATCACTCTG ACCATAATCA TGCTGCTTCT GGTAAAAATA

AGCGAAAAGC TCTTTGCCCA GACCATGACT CAGATAGTTC AGGTAAAGAT CCTAGAAACA

GCCAGGGGAA AGGAGCTCAC CGACCAGAAC ATGCCAGTGG TAGAAGGAAT GTCAAGGACA

GTGTTAGTGC TAGTGAAGTG ACCTCAACTG TGTACAACAC TGTCTCTGAA GGAACTCACT

TTCTAGAGAC AATAGAGACT CCAAGACCTG GAAAACTCTT CCCCAAAGAT GTAAGCAGCT

CCACTCCACC CAGTGTCACA TCAAAGAGCC GGGTGAGCCG GCTGGCTGGT AGGAAAACAA

ATGAATCTGT GAGTGAGCCC CGAAAAGGCT TTATGTATTC CAGAAACACA AATGAAAATC

CTCAGGAGTG TTTCAATGCA TCAAAGCTAC TGACATCTCA TGGCATGGGC ATCCAGGTTC

CGCTGAATGC AACAGAGTTC AACTATCTCT GTCCAGCCAT CATCAACCAA ATTGATGCTA

GATCTTGTCT GATTCATACA AGTGAAAAGA AGGCTGAAAT CCCTCCAAAG ACCTATTCAT

TACAAATAGC CTGGGTTGGT GGTTTTATAG CCATTTCCAT CATCAGTTTC CTGTCTCTGC

TGGGGGTTAT CTTAGTGCCT CTCATGAATC GGGTGTTTTT CAAATTTCTC CTGAGTTTCC

TTGTGGCACT GGCCGTTGGG ACTTTGAGTG GTGATGCTTT TTTACACCTT CTTCCACATT

CTCATGCAAG TCACCACCAT AGTCATAGCC ATGAAGAACC AGCAATGGAA ATGAAAAGAG

GACCACTTTT CAGTCATCTG TCTTCTCAAA ACATAGAAGA AAGTGCCTAT TTTGATTCCA

CGTGGAAGGG TCTAACAGCT CTAGGAGGCC TGTATTTCAT GTTTCTTGTT GAACATGTCC

TCACATTGAT CAAACAATTT AAAGATAAGA AGAAAAAGAA TCAGAAGAAA CCTGAAAATG

ATGATGATGT GGAGATTAAG AAGCAGTTGT CCAAGTATGA ATCTCAACTT TCAACAAATG

TABLE 1-continued

DNA AND PROTEIN SEQUENCES OF LIV-1
(GENBANK ACCESSION NM_012319)

AGGAGAAAGT AGATACAGAT GATCGAACTG AAGGCTATTT ACGAGCAGAC TCACAAGAGC

CCTCCCACTT TGATTCTCAG CAGCCTGCAG TCTTGGAAGA AGAAGAGGTC ATGATAGCTC

ATGCTCATCC ACAGGAAGTC TACAATGAAT ATGTACCCAG AGGGTGCAAG AATAAATGCC

ATTCACATTT CCACGATACA CTCGGCCAGT CAGACGATCT CATTCACCAC CATCATGACT

ACCATCATAT TCTCCATCAT CACCACCACC AAAACCACCA TCCTCACAGT CACAGCCAGC

GCTACTCTCG GGAGGAGCTG AAAGATGCCG GCGTCGCCAC TTTGGCCTGG ATGGTGATAA

TGGGTGATGG CCTGCACAAT TTCAGCGATG GCCTAGCAAT TGGTGCTGCT TTTACTGAAG

GCTTATCAAG TGGTTTAAGT ACTTCTGTTG CTGTGTTCTG TCATGAGTTG CCTCATGAAT

TAGGTGACTT TGCTGTTCTA CTAAAGGCTG GCATGACCGT TAAGCAGGCT GTCCTTTATA

ATGCATTGTC AGCCATGCTG GCGTATCTTG GAATGGCAAC AGGAATTTTC ATTGGTCATT

ATGCTGAAAA TGTTTCTATG TGGATATTTG CACTTACTGC TGGCTTATTC ATGTATGTTG

CTCTGGTTGA TATGGTACCT GAAATGCTGC ACAATGATGC TAGTGACCAT GGATGTAGCC

GCTGGGGGTA TTTCTTTTTA CAGAATGCTG GGATGCTTTT GGGTTTTGGA ATTATGTTAC

TTATTTCCAT ATTTGAACAT AAAATCGTGT TTCGTATAAA TTTCTAGTTA AGGTTTAAAT

GCTAGAGTAG CTTAAAAAGT TGTCATAGTT TCAGTAGGTC ATAGGGAGAT GAGTTTGTAT

GCTGTACTAT GCAGCGTTTA AAGTTAGTGG GTTTTGTGAT TTTTGTATTG AATATTGCTG

TCTGTTACAA AGTCAGTTAA AGGTACGTTT TAATATTTAA GTTATTCTAT CTTGGAGATA

AAATCTGTAT GTGCAATTCA CCGGTATTAC CAGTTTATTA TGTAAACAAG AGATTTGGCA

TGACATGTTC TGTATGTTTC AGGGAAAAAT GTCTTTAATG CTTTTTCAAG AACTAACACA

GTTATTCCTA TACTGGATTT TAGGTCTCTG AAGAACTGCT GGTG

SEQ ID NO: 2
LIV-1 PROTEIN SEQUENCE

MARKLSVILILTFALSVTNPLHELKAAAFPQTTEKISPNWESGINVDLAISTRQYHLQQLFYRY

GENNSLSVEGFRKLLQNIGIDKIKRIHIHHDHDHHSDHEHHSDHERHSDHEHHSDHEHHSDHNH

AASGKNKRKALCPDHDSDSSGKDPRNSQGKGAHRPEHASGRRNVKDSVSASEVTSTVYNTVSEG

THFLETIETPRPGKLFPKDVSSSTPPSVTSKSRVSRLAGRKTNESVSEPRKGFMYSRNTNENPQ

ECFNASKLLTSHGMGIQVPLNATEFNYLCPAIINQIDARSCLIHTSEKKAEIPPKTYSLQIAWV

GGFIAISIISFLSLLGVILVPLMNRVFFKFLLSFLVALAVGTLSGDAFLHLLPHSHASHHHSHS

HEEPAMEMKRGPLFSHLSSQNIEESAYFDSTWKGLTALGGLYFMFLVEHVLTLIKQFKDKKKKN

QKKPENDDDVEIKKQLSKYESQLSTNEEKVDTDDRTEGYLRADSQEPSHFDSQQPAVLEEEEVM

IAHAHPQEVYNEYVPRGCKNKCHSHFHDTLGQSDDLIHHHHDYHHILHHHHHQNHHPHSHSQRY

SREELKDAGVATLAWMVIMGDGLHNFSDGLAIGAAFTEGLSSGLSTSVAVFCHELPHELGDFAV

LLKAGMTVKQAVLYNALSAMLAYLGMATGIFIGHYAENVSMWIFALTAGLFMYVALVDMVPEML

HNDASDHGCSRWGYFFLQNAGMLLGFGIMLLISIFEHKIVFRINF

TABLE 2

ANTI-LIV-1 #1.7A4 DNA AND PEPTIDE SEQUENCES

PROTEIN SEQUENCES

SEQ ID NO: 3

Heavy chain variable domain; CDRs in bold and underlined:

eiqlqqsgpelmkpgasvkisckastysftryfmhwvkqshgeslewigyidpfnggtgynqkfkgkatltvdkssstaymhlssl tsedsavyycvtygsdyfdywgqgttltvss

SEQ ID NO: 4

Light chain variable domain; CDRs in bold and underlined:

divmtqpqkfmstsvgdrvsvtckasqnvetdvvwyqqkpgqppkaliysasyrhsgvpdrftgsgsgtnftltistvqsedlaeyf cqqynnypftfgsgtkleiir

DNA SEQUENCES

SEQ ID NO: 5

Heavy chain variable domain:

GAGATCCAGCTGCAGCAGTCTGGACCTGAGCTGATGAAGCCTGGGGCTTCAGTGAAGATATCTT

GCAAGGCTTCTACTTACTCATTCACTAGGTACTTCATGCACTGGGTGAAGCAGAGCCATGGAGA

GAGCCTTGAGTGGATTGGATATATTGATCCTTTCAATGGTGGTACTGGCTACAATCAGAAATTC

AAGGGCAAGGCCACATTGACTGTAGACAAATCTTCCAGCACAGCCTACATGCATCTCAGCAGCC

TGACATCTGAGGACTCTGCAGTCTATTACTGTGTAACGTATGGCTCCGACTACTTTGACTATTG

GGGCCAAGGCACCACTCTCACAGTCTCCTCA

SEQ ID NO: 6

LIGHT CHAIN VARIABLE DOMAIN:

GACATTGTGATGACCCAGCCACAAAAATTCATGTCCACGTCTGTAGGCGACAGGGTCAGTGTCA

CCTGCAAGGCCAGTCAGAATGTGGAAACTGATGTAGTCTGGTATCAACAGAAACCTGGGCAACC

ACCTAAAGCACTGATTTACTCGGCATCCTACCGGCACAGTGGAGTCCCTGATCGCTTCACAGGC

AGTGGATCTGGGACAAATTTCACTCTCACCATCAGCACTGTACAGTCTGAAGACTTGGCAGAGT

ATTTCTGTCAGCAATATAACAACTATCCATTCACGTTCGGCTCGGGGACAAAGTTGGAAATAAT

ACGG

| TABLE 3 |
|---|
| Lists Of Medical Conditions |
| LIV-1 has been found to be over-expressed in cancers of the organs listed in the Table. Therefore, targeting or inhibiting LIV-1, by any means known in the art, including but limited to antibodies, may be a an effective treatment for such diseases.<br>bladder: carcinoma in situ, papillary carcinomas, transitional cell carcinoma, squamous cell carcinoma<br>breast: ductal carcinoma in situ, lobular carcinoma in situ<br>ovary: ovarian carcinoma (e.g., epithelial (serous tumors, mucinous tumors, endometrioid tumors), germ cell (e.g., teratomas, choriocarcinomas, polyembryomas, embryomal carcinoma, endodermal sinus tumor, dysgerminoma, gonadoblastoma), stromal carcinomas (e.g., granulosal stromal cell tumors)), fallopian tube carcinoma, peritoneal carcinoma, leiomyoma<br>prostate: epithelial neoplasms (e.g., adenocarcinoma, small cell tumors, transitional cell carcinoma, carcinoma in situ, and basal cell carcinoma), carcinosarcoma, non-epithelial neoplasms (e.g., mesenchymal and lymphoma), germ cell tumors, prostatic intraepithelial neoplasia (PIN), hormone independent prostate cancer, benign prostate hyperplasia, prostatitis |

| TABLE 4 |
|---|
| Cell Lines For Validating Liv-1 Antibodies<br>For Bladder And Ovarian Cancers: |
| The following cell lines may be used to validate the effectiveness of anti-LIV-1 antibodies in diseases involving ovaries and bladder. Experiments similar to those described in the Examples above, could be carried out.<br>SW780 (bladder), OVCAR3 (ovarian), ES-2 (ovarian). |

It is understood that the examples described above in no way serve to limit the true scope of this invention, but rather are presented for illustrative purposes. All publications, sequences of accession numbers, and patent applications cited in this specification are herein incorporated by reference as if each individual publication or patent application were specifically and individually indicated to be incorporated by reference.

All UniGene cluster identification numbers and accession numbers herein are for the GenBank sequence database and the sequences of the accession numbers are hereby expressly incorporated by reference. GenBank is known in the art, see, e.g., Benson, D A, et al., Nucleic Acids Research 26:1-7 (1998). Sequences are also available in other databases, e.g., European Molecular Biology Laboratory (EMBL) and DNA Database of Japan (DDBJ).

TABLE 5

Liv-1 Mutant BCR4M1 cDNA and Protein Sequences

BCR4 M1 cDNA (SEQ ID NO: 13)

ATGGCGAGGAAGTTATCTGTAATCTTGATCCTGACCTTTGCCCTCTCTGTCACAAATCCCCTTCATGAAC
TAAAAGCAGCTGCTTTCCCCCAGACCACTGAGAAAATTAGTCCGAATTGGGAATCTGGCATTAATGTTGA
CTTGGCAATTTCCACACGGCAATATCATCTACAACAGCTTTTCTACCGCTATGGAGAAAATAATTCTTTG
TCAGTTGAAGGGTTCAGAAAATTACTTCAAAATATAGGCATAGATAAGATTAAAAGAATCCATATACACC
ATGACCACGACCATCACTCAGACCACGAGCATCACTCAGACCATGAGCGTCACTCAGACCATGAGCATCA
CTCAGACCACGAGCATCACTCTGACCATGATCATCACTCTCACCATAATCATGCTGCTTCTGGTAAAAAT
AAGCGAAAAGCTCTTTGCCCAGACCATGACTCAGATAGTTCAGGTAAAGATCCTAGAAACAGCCAGGGGA
AAGGAGCTCACCGACCAGAACATGCCAGTGGTAGAAGGAATGTCAAGGACAGTGTTAGTGCTAGTGAAGT
GACCTCAACTGTGTACAACACTGTCTCTGAAGGAACTCACTTTCTAGAGACAATAGAGACTCCAAGACCT
GGAAAACTCTTCCCCAAAGATGTAAGCAGCTCCACTCCACCCAGTGTCACATCAAAGAGCCGGGTGAGCC
GGCTGGCTGGTAGGAAAACAAATGAATCTGTGAGTGAGCCCCGAAAAGGCTTTATGTATTCCAGAAACAC
AAATGAAAATCCTCAGGAGTGTTTCAATGCATCAAAGCTACTGACATCTCATGGCATGGGCATCCAGGTT
CCGCTGAATGCAACAGAGTTCAACTATCTCTGTCCAGCCATCATCAACCAAATTGATGCTAGATCTTGTC
TGATTCATACAAGTGAAAAGAAGGCTGAAATCCCTCCAAAGACCTATTCATTACAAATAGCCTGGGTTGG
TGGTTTTATAGCCATTTCCATCATCAGTTTCCTGTCTCTGCTGGGGGTTATCTTAGTGCCTCTCATGAAT
CGGGTGTTTTTCAAATTTCTCCTGAGTTTCCTTGTGGCACTGGCCGTTGGGACTTTGAGTGGTGATGCTT
TTTTACACCTTCTTCCACATTCTCATGCAAGTCACCACCATAGTCATAGCCATGAAGAACCAGCAATGGA
AATGAAAAGAGGACCACTTTTCAGTCATCTGTCTTCTCAAAACATAGAAGAAAGTGCCTATTTTGATTCC
ACGTGGAAGGGTCTAACAGCTCTAGGAGGCCTGTATTTCATGTTTCTTGTTGAACATGTCCTCACATTGA
TCAAACAATTTAAAGATAAGAAGAAAAAGAATCAGAAGAAACCTGAAAATGATGATGATGTGGAGATTAA
GAAGCAGTTGTCCAAGTATGAATCTCAACTTTCAACAAATGAGGAGAAAGTAGATACAGATGATCGAACT
GAAGGCTATTTACGAGCAGACTCACAAGAGCCCTCCCACTTTGATTCTCAGCAGCCTGCAGTCTTGGAAG
AAGAAGAGGTCATGATAGCTCATGCTCATCCACAGGAAGTCTACAATGAATATGTACCCAGAGGGTGCAA
GAATAAATGCCATTCACATTTCCACGATACACTCGGCCAGTCAGACGATCTCATTCACCACCATCATGAC
TACCATCATATTCTCCATCATCACCACCACCAAAACCACCATCCTCACAGTCACAGCCAGCGCTACTCTC
GGGAGGAGCTGAAAGATGCCGGCGTCGCCACTTTGGCCTGGATGGTGATAATGGGTGATGGCCTGCACAA
TTTCAGCGATGGCCTAGCAATTGGTGCTGCTTTTACTGAAGGCTTATCAAGTGGTTTAAGTACTTCTGTT
GCTGTGTTCTGTGCTGCGTTGCCTGCTGCATTAGGTGACTTTGCTGTTCTACTAAAGGCTGGCATGACCG
TTAAGCAGGCTGTCCTTTATAATGCATTGTCAGCCATGCTGGCGTATCTTGGAATGGCAACAGGAATTTT
CATTGGTCATTATGCTGAAAATGTTTCTATGTGGATATTGCACTTACTGCTGGCTTATTCATGTATGTT
GCTCTGGTTGATATGGTACCTGAAATGCTGCACAATGATGCTAGTGACCATGGATGTAGCCGCTGGGGGT
ATTTCTTTTTACAGAATGCTGGGATGCTTTTGGGTTTTGGAATTATGTTACTTATTTCCATATTTGAACA
TAAAAATCGTGTTTCGTATAAATTTC

BCR4 M1 protein sequence (SEQ ID NO: 14)
MARKLSVILILTFALSVTNPLHELKAAAFPQTTEKISPNWESGINVDLAISTRQYHLQQLFYRYGENNSL
SVEGFRKLLQNIGIDKIKRIHIHHDHDHHSDHEHHSDHERHSDHEHHSDHEHHSDHDHHSHHNHAASGKN
KRKALCPDHDSDSSGKDPRNSQGKGAHRPEHASGRRNVKDSVSASEVTSTVYNTVSEGTHFLETIETPRP TABLE 5-continued Liv-1 Mutant BCR4M1 cDNA and Protein Sequences

GKLFPKDVSSSTPPSVTSKSRVSRLAGRKTNESVSEPRKGFMYSRNTNENPQECFNASKLLTSHGMGIQV

PLNATEFNYLCPAIINQIDARSCLIHTSEKKAEIPPKTYSLQIAWVGGFIAISIISFLSLLGVILVPLMN

RVFFKFLLSFLVALAVGTLSGDAFLHLLPHSHASHHHSHSHEEPAMEMKRGPLFSHLSSQNIEESAYFDS

TWKGLTALGGLYFMFLVEHVLTLIKQFKDKKKKNQKKPENDDDVEIKKQLSKYESQLSTNEEKVDTDDRT

EGYLRADSQEPSHFDSQQPAVLEEEEVMIAHAHPQEVYNEYVPRGCKNKCHSHFHDTLGQSDDLIHHHHD

YHHILHHHHHQNHHPHSHSQRYSREELKDAGVATLAWMVIMGDGLHNFSDGLAIGAAFTEGLSSGLSTSV

AVFCAALPAALGDFAVLLKAGMTVKQAVLYNALSAMLAYLGMATGIFIGHYAENVSMWIFALTAGLFMYV

ALVDMVPEMLHNDASDHGCSRWGYFFLQNAGMLLGFGIMLLISIFEHKIVFRINF

TABLE 6

Liv-1 Antibodies

| Number | Designation |
|---|---|
| 1 | 1.1F10 |
| 2 | 1.7A4 |
| 3 | BR2-10b |
| 4 | BR2-11a |
| 5 | BR2-13a |
| 6 | BR2-14a |
| 7 | BR2-15a |
| 8 | BR2-16a |
| 9 | BR2-17a |
| 10 | BR2-18a |
| 11 | BR2-19a |
| 12 | BR2-20a |
| 13 | BR2-21a |
| 14 | BR2-22a |
| 15 | BR2-23a |
| 16 | BR2-24a |
| 17 | BR2-25a |

ATCC DEPOSIT

Under the terms of the Budapest Treaty on the International Recognition of the Deposit of Microorganisms for the Purpose of Patent Procedure, the hybridomas that produce antibodies BR2-14a, BR2-19a, BR2-22a, and BR2-23a (aka antibodies 14, 19, 22, and 23, respectively) were deposited with the American Type Culture Collection (ATCC). The deposit of the hybridomas that produce antibodies BR2-14a, BR2-19a, and BR2-23a, were deposited on Dec. 19, 2003 and accorded accession numbers PTA-5705, PTA-5706, and PTA-5707, respectively. The hybridoma that produces antibody BR2-22a was deposited on Nov. 11, 2010 and accorded accession number PTA-11478. The ATCC is located at 10801 University Boulevard, Manassas, Va. 20110-2209, USA.

What is claimed is:

1. A monoclonal antibody that specifically binds to a protein having the amino acid sequence of SEQ ID NO:2, wherein the antibody is selected from the group consisting of BR2-14a, which is produced by the hybridoma having ATCC accession number PTA-5705, BR2-19a, which is produced by the hybridoma having ATCC accession number PTA-5706, BR2-22a, which is produced by the hybridoma having ATCC accession number PTA-11478, and BR2-23a, which is produced by the hybridoma having ATCC accession number PTA-5707, or a chimeric or humanized form thereof.

2. The antibody of claim 1, wherein the antibody is a humanized form of the antibody.

3. The antibody of claim 1, wherein the antibody is a humanized form of BR2-14a.

4. The antibody of claim 1, wherein the antibody is a humanized form of BR2-19a.

5. The antibody of claim 1, wherein the antibody is a humanized form of BR2-23a.

6. The antibody of claim 1, wherein the antibody is an antigen-binding fragment.

7. The antibody of claim 1, wherein the antibody is conjugated to an effector component.

8. The antibody of claim 7, wherein the effector component is selected from the group consisting of a fluorescent label, a radioisotope or a cytotoxic chemical.

9. The antibody of claim 8, wherein the cytotoxic chemical is auristatin-E or monomethyl auristatin E.

10. A pharmaceutical composition comprising a pharmaceutically acceptable excipient and the antibody of claim 1.

11. The pharmaceutical composition of claim 10, wherein the antibody is an antigen-binding fragment.

12. The pharmaceutical composition of claim 10, wherein the antibody is conjugated to an effector component comprising a radioisotope or a cytotoxic chemical.

13. The pharmaceutical composition of claim 12, wherein the cytotoxic chemical is auristatin-E or monomethyl auristatin E.

14. A hybridoma having ATCC Accession No. PTA-5705.

15. A hybridoma having ATCC Accession No. PTA-5706.

16. A hybridoma having ATCC Accession No. PTA-5707.

17. A hybridoma having ATCC Accession No. PTA-11478.

18. The antibody of claim 1, wherein the antibody is the humanized form of BR2-22a.

* * * * *

SEQUENCE LISTING

<160> NUMBER OF SEQ ID NOS: 18

<210> SEQ ID NO 1
<211> LENGTH: 2744
<212> TYPE: DNA
<213> ORGANISM: Homo sapiens

<400> SEQUENCE: 1

```
ctcgtgccga attcggcacg agaccgcgtg ttcgcgcctg gtagagattt ctcgaagaca      60
ccagtgggcc cgtgtggaac caaacctgcg cgcgtggccg ggccgtggga caacgaggcc     120
gcggagacga aggcgcaatg gcgaggaagt tatctgtaat cttgatcctg acctttgccc     180
tctctgtcac aaatcccctt catgaactaa aagcagctgc tttcccccag accactgaga     240
aaattagtcc gaattgggaa tctggcatta atgttgactt ggcaatttcc acacggcaat     300
atcatctaca acagcttttc taccgctatg gagaaaataa ttctttgtca gttgaagggt     360
tcagaaaatt acttcaaaat ataggcatag ataagattaa aagaatccat atacaccatg     420
accacgacca tcactcagac cacgagcatc actcagacca tgagcgtcac tcagaccatg     480
agcatcactc agaccacgag catcactctg accataatca tgctgcttct ggtaaaaata     540
agcgaaaagc tctttgccca gaccatgact cagatagttc aggtaaagat cctagaaaca     600
```

```
gccaggggaa aggagctcac cgaccagaac atgccagtgg tagaaggaat gtcaaggaca      660
gtgttagtgc tagtgaagtg acctcaactg tgtacaacac tgtctctgaa ggaactcact      720
ttctagagac aatagagact ccaagacctg gaaaactctt ccccaaagat gtaagcagct      780
ccactccacc cagtgtcaca tcaaagagcc gggtgagccg gctggctggt aggaaaacaa      840
atgaatctgt gagtgagccc cgaaaaggct ttatgtattc cagaaacaca atgaaaatc       900 ctcaggagtg tttcaatgca tcaaagctac tgacatctca tggcatgggc atccaggttc      960
cgctgaatgc aacagagttc aactatctct gtccagccat catcaaccaa attgatgcta     1020
gatcttgtct gattcataca agtgaaaaga aggctgaaat ccctccaaag acctattcat     1080
tacaaatagc ctgggttggt ggttttatag ccatttccat catcagtttc ctgtctctgc     1140
tgggggttat cttagtgcct ctcatgaatc gggtgttttt caaatttctc ctgagtttcc     1200
ttgtggcact ggccgttggg actttgagtg gtgatgcttt tttacacctt cttccacatt     1260
ctcatgcaag tcaccaccat agtcatagcc atgaagaacc agcaatggaa atgaaaagag     1320
gaccactttt cagtcatctg tcttctcaaa acatagaaga aagtgcctat tttgattcca     1380
cgtggaaggg tctaacagct ctaggaggcc tgtatttcat gtttcttgtt gaacatgtcc     1440
tcacattgat caaacaattt aaagataaga agaaaaagaa tcagaagaaa cctgaaaatg     1500
atgatgatgt ggagattaag aagcagttgt ccaagtatga atctcaactt tcaacaaatg     1560
aggagaaagt agatacagat gatcgaactg aaggctattt acgagcagac tcacaagagc     1620
cctcccactt tgattctcag cagcctgcag tcttggaaga agaagaggtc atgatagctc     1680
atgctcatcc acaggaagtc tacaatgaat atgtacccag agggtgcaag aataaatgcc     1740
attcacattt ccacgataca ctcggccagt cagacgatct cattcaccac catcatgact     1800
accatcatat tctccatcat caccaccacc aaaaccacca tcctcacagt cacagccagc     1860
gctactctcg ggaggagctg aaagatgccg gcgtcgccac tttggcctgg atggtgataa     1920
tgggtgatgg cctgcacaat ttcagcgatg gcctagcaat tggtgctgct tttactgaag     1980
gcttatcaag tggtttaagt acttctgttg ctgtgttctg tcatgagttg cctcatgaat     2040
taggtgactt tgctgttcta ctaaaggctg gcatgaccgt taagcaggct gtcctttata     2100
atgcattgtc agccatgctg gcgtatcttg gaatggcaac aggaattttc attggtcatt     2160
atgctgaaaa tgtttctatg tggatatttg cacttactgc tggcttattc atgtatgttg     2220
ctctggttga tatggtacct gaaatgctgc acaatgatgc tagtgaccat ggatgtagcc     2280
gctgggggta tttctttttta cagaatgctg ggatgctttt gggttttgga attatgttac     2340
ttatttccat atttgaacat aaaatcgtgt ttcgtataaa tttctagtta aggtttaaat     2400
gctagagtag cttaaaaagt tgtcatagtt tcagtaggtc atagggagat gagtttgtat     2460
gctgtactat gcagcgttta aagttagtgg gttttgtgat ttttgtattg aatattgctg     2520
tctgttacaa agtcagttaa aggtacgttt taatatttaa gttattctat cttggagata     2580
aaatctgtat gtgcaattca ccggtattac cagtttatta tgtaaacaag agatttggca     2640
tgacatgttc tgtatgtttc agggaaaaat gtctttaatg cttttttcaag aactaacaca     2700 gttattccta tactggattt taggtctctg aagaactgct ggtg                       2744
```

<210> SEQ ID NO 2
<211> LENGTH: 749
<212> TYPE: PRT
<213> ORGANISM: Homo sapiens

<400> SEQUENCE: 2

-continued

```
Met Ala Arg Lys Leu Ser Val Ile Leu Ile Leu Thr Phe Ala Leu Ser
 1               5                  10                  15

Val Thr Asn Pro Leu His Glu Leu Lys Ala Ala Phe Pro Gln Thr
             20                  25                  30

Thr Glu Lys Ile Ser Pro Asn Trp Glu Ser Gly Ile Asn Val Asp Leu
             35                  40                  45

Ala Ile Ser Thr Arg Gln Tyr His Leu Gln Gln Leu Phe Tyr Arg Tyr
         50                  55                  60

Gly Glu Asn Asn Ser Leu Ser Val Glu Gly Phe Arg Lys Leu Leu Gln
 65                  70                  75                  80

Asn Ile Gly Ile Asp Lys Ile Lys Arg Ile His Ile His His Asp His
                 85                  90                  95

Asp His His Ser Asp His Glu His Ser Asp His Glu Arg His Ser
             100                 105                 110

Asp His Glu His His Ser Asp His Glu His His Ser Asp His Asn His
         115                 120                 125

Ala Ala Ser Gly Lys Asn Lys Arg Lys Ala Leu Cys Pro Asp His Asp
         130                 135                 140

Ser Asp Ser Ser Gly Lys Asp Pro Arg Asn Ser Gln Gly Lys Gly Ala
145                 150                 155                 160

His Arg Pro Glu His Ala Ser Gly Arg Arg Asn Val Lys Asp Ser Val
                 165                 170                 175

Ser Ala Ser Glu Val Thr Ser Thr Val Tyr Asn Thr Val Ser Glu Gly
             180                 185                 190

Thr His Phe Leu Glu Thr Ile Glu Thr Pro Arg Pro Gly Lys Leu Phe
         195                 200                 205

Pro Lys Asp Val Ser Ser Thr Pro Ser Val Thr Ser Lys Ser
         210                 215                 220

Arg Val Ser Arg Leu Ala Gly Arg Lys Thr Asn Glu Ser Val Ser Glu
225                 230                 235                 240

Pro Arg Lys Gly Phe Met Tyr Ser Arg Asn Thr Asn Glu Asn Pro Gln
                 245                 250                 255

Glu Cys Phe Asn Ala Ser Lys Leu Leu Thr Ser His Gly Met Gly Ile
             260                 265                 270

Gln Val Pro Leu Asn Ala Thr Glu Phe Asn Tyr Leu Cys Pro Ala Ile
         275                 280                 285

Ile Asn Gln Ile Asp Ala Arg Ser Cys Leu Ile His Thr Ser Glu Lys
         290                 295                 300

Lys Ala Glu Ile Pro Pro Lys Thr Tyr Ser Leu Gln Ile Ala Trp Val
305                 310                 315                 320

Gly Gly Phe Ile Ala Ile Ser Ile Ile Ser Phe Leu Ser Leu Leu Gly
                 325                 330                 335

Val Ile Leu Val Pro Leu Met Asn Arg Val Phe Phe Lys Phe Leu Leu
             340                 345                 350

Ser Phe Leu Val Ala Leu Ala Val Gly Thr Leu Ser Gly Asp Ala Phe
         355                 360                 365

Leu His Leu Leu Pro His Ser His Ala Ser His His His Ser His Ser
         370                 375                 380

His Glu Glu Pro Ala Met Glu Met Lys Arg Gly Pro Leu Phe Ser His
385                 390                 395                 400

Leu Ser Ser Gln Asn Ile Glu Glu Ser Ala Tyr Phe Asp Ser Thr Trp
                 405                 410                 415

Lys Gly Leu Thr Ala Leu Gly Gly Leu Tyr Phe Met Phe Leu Val Glu
```

```
                        420                 425                 430
His Val Leu Thr Leu Ile Lys Gln Phe Lys Asp Lys Lys Lys Asn
            435                 440                 445
Gln Lys Lys Pro Glu Asn Asp Asp Val Glu Ile Lys Lys Gln Leu
            450                 455                 460
Ser Lys Tyr Glu Ser Gln Leu Ser Thr Asn Glu Glu Lys Val Asp Thr
465                 470                 475                 480
Asp Asp Arg Thr Glu Gly Tyr Leu Arg Ala Asp Ser Gln Glu Pro Ser
                485                 490                 495
His Phe Asp Ser Gln Gln Pro Ala Val Leu Glu Glu Glu Val Met
            500                 505                 510
Ile Ala His Ala His Pro Gln Glu Val Tyr Asn Glu Tyr Val Pro Arg
            515                 520                 525
Gly Cys Lys Asn Lys Cys His Ser His Phe His Asp Thr Leu Gly Gln
            530                 535                 540
Ser Asp Asp Leu Ile His His His Asp Tyr His His Ile Leu His
545                 550                 555                 560
His His His His Gln Asn His His Pro His Ser His Ser Gln Arg Tyr
                565                 570                 575
Ser Arg Glu Glu Leu Lys Asp Ala Gly Val Ala Thr Leu Ala Trp Met
            580                 585                 590
Val Ile Met Gly Asp Gly Leu His Asn Phe Ser Asp Gly Leu Ala Ile
            595                 600                 605
Gly Ala Ala Phe Thr Glu Gly Leu Ser Ser Gly Leu Ser Thr Ser Val
            610                 615                 620
Ala Val Phe Cys His Glu Leu Pro His Glu Leu Gly Asp Phe Ala Val
625                 630                 635                 640
Leu Leu Lys Ala Gly Met Thr Val Lys Gln Ala Val Leu Tyr Asn Ala
                645                 650                 655
Leu Ser Ala Met Leu Ala Tyr Leu Gly Met Ala Thr Gly Ile Phe Ile
            660                 665                 670
Gly His Tyr Ala Glu Asn Val Ser Met Trp Ile Phe Ala Leu Thr Ala
            675                 680                 685
Gly Leu Phe Met Tyr Val Ala Leu Val Asp Met Val Pro Glu Met Leu
            690                 695                 700
His Asn Asp Ala Ser Asp His Gly Cys Ser Arg Trp Gly Tyr Phe Phe
705                 710                 715                 720
Leu Gln Asn Ala Gly Met Leu Leu Gly Phe Gly Ile Met Leu Leu Ile
                725                 730                 735
Ser Ile Phe Glu His Lys Ile Val Phe Arg Ile Asn Phe
            740                 745

<210> SEQ ID NO 3
<211> LENGTH: 117
<212> TYPE: PRT
<213> ORGANISM: Mus musculus

<400> SEQUENCE: 3

Glu Ile Gln Leu Gln Gln Ser Gly Pro Glu Leu Met Lys Pro Gly Ala
1               5                   10                  15
Ser Val Lys Ile Ser Cys Lys Ala Ser Thr Tyr Ser Phe Thr Arg Tyr
                20                  25                  30
Phe Met His Trp Val Lys Gln Ser His Gly Glu Ser Leu Glu Trp Ile
            35                  40                  45
Gly Tyr Ile Asp Pro Phe Asn Gly Gly Thr Gly Tyr Asn Gln Lys Phe
```

```
            50                  55                  60
Lys Gly Lys Ala Thr Leu Thr Val Asp Lys Ser Ser Thr Ala Tyr
 65                  70                  75                  80

Met His Leu Ser Ser Leu Thr Ser Glu Asp Ser Ala Val Tyr Tyr Cys
                 85                  90                  95

Val Thr Tyr Gly Ser Asp Tyr Phe Asp Tyr Trp Gly Gln Gly Thr Thr
                100                 105                 110

Leu Thr Val Ser Ser
        115

<210> SEQ ID NO 4
<211> LENGTH: 108
<212> TYPE: PRT
<213> ORGANISM: Mus musculus

<400> SEQUENCE: 4

Asp Ile Val Met Thr Gln Pro Gln Lys Phe Met Ser Thr Ser Val Gly
 1               5                  10                  15

Asp Arg Val Ser Val Thr Cys Lys Ala Ser Gln Asn Val Glu Thr Asp
                20                  25                  30

Val Val Trp Tyr Gln Gln Lys Pro Gly Gln Pro Pro Lys Ala Leu Ile
             35                  40                  45

Tyr Ser Ala Ser Tyr Arg His Ser Gly Val Pro Asp Arg Phe Thr Gly
         50                  55                  60

Ser Gly Ser Gly Thr Asn Phe Thr Leu Thr Ile Ser Thr Val Gln Ser
 65                  70                  75                  80

Glu Asp Leu Ala Glu Tyr Phe Cys Gln Gln Tyr Asn Asn Tyr Pro Phe
                 85                  90                  95

Thr Phe Gly Ser Gly Thr Lys Leu Glu Ile Ile Arg
                100                 105

<210> SEQ ID NO 5
<211> LENGTH: 351
<212> TYPE: DNA
<213> ORGANISM: Mus musculus

<400> SEQUENCE: 5
gagatccagc tgcagcagtc tggacctgag ctgatgaagc ctggggcttc agtgaagata      60
tcttgcaagg cttctactta ctcattcact aggtacttca tgcactgggt gaagcagagc     120
catggagaga gccttgagtg gattggatat attgatcctt caatggtgga tactggctac     180
aatcagaaat tcaagggcaa ggccacattg actgtagaca atcttccag cacagcctac      240 atgcatctca gcagcctgac atctgaggac tctgcagtct attactgtgt aacgtatggc     300
tccgactact tgactattg gggccaaggc accactctca cagtctcctc a               351

<210> SEQ ID NO 6
<211> LENGTH: 324
<212> TYPE: DNA
<213> ORGANISM: Mus musculus

<400> SEQUENCE: 6
gacattgtga tgacccagcc acaaaaattc atgtccacgt ctgtaggcga cagggtcagt      60
gtcacctgca aggccagtca gaatgtggaa actgatgtag tctggtatca acagaaacct     120
gggcaaccac ctaaagcact gatttactcg gcatcctacc ggcacagtgg agtccctgat     180
cgcttcacag gcagtggatc tgggacaaat ttcactctca ccatcagcac tgtacagtct     240
gaagacttgg cagagtattt ctgtcagcaa tataacaact atccattcac gttcggctcg     300
```
gggacaaagt tggaaataat acgg                                          324

<210> SEQ ID NO 7
<211> LENGTH: 21
<212> TYPE: DNA
<213> ORGANISM: Artificial Sequence
<220> FEATURE:
<223> OTHER INFORMATION: H2R1 sense siRNA control

<400> SEQUENCE: 7
cagacacggc cacgugugat t                                             21

<210> SEQ ID NO 8
<211> LENGTH: 21
<212> TYPE: DNA
<213> ORGANISM: Artificial Sequence
<220> FEATURE:
<223> OTHER INFORMATION: H2R1 antisense siRNA control

<400> SEQUENCE: 8
ucacacgugg ccgugucugt t                                             21

<210> SEQ ID NO 9
<211> LENGTH: 21
<212> TYPE: DNA
<213> ORGANISM: Artificial Sequence
<220> FEATURE:
<223> OTHER INFORMATION: HKSP-1 positive control siRNA

<400> SEQUENCE: 9
gcuagcgccc auucaauagt t                                             21

<210> SEQ ID NO 10
<211> LENGTH: 21
<212> TYPE: DNA
<213> ORGANISM: Artificial Sequence
<220> FEATURE:
<223> OTHER INFORMATION: HKSP-1 antisense positive control siRNA

<400> SEQUENCE: 10
cuauugaaug ggcgcuagct t                                             21

<210> SEQ ID NO 11
<211> LENGTH: 21
<212> TYPE: DNA
<213> ORGANISM: Artificial Sequence
<220> FEATURE:
<223> OTHER INFORMATION: BCR4-53 sense siRNA

<400> SEQUENCE: 11
cagcuuuucu accgcuaugt t                                             21

<210> SEQ ID NO 12
<211> LENGTH: 21
<212> TYPE: DNA
<213> ORGANISM: Artificial Sequence
<220> FEATURE:
<223> OTHER INFORMATION: BCR4-53 antisense siRNA

<400> SEQUENCE: 12
cauagcggua gaaaagcugt t                                             21

<210> SEQ ID NO 13
<211> LENGTH: 2265
<212> TYPE: DNA
<213> ORGANISM: Artificial Sequence
<220> FEATURE:
<223> OTHER INFORMATION: BCR4 mutant cDNA

<400> SEQUENCE: 13

```
atggcgagga agttatctgt aatcttgatc ctgacctttg ccctctctgt cacaaatccc      60
cttcatgaac taaaagcagc tgctttcccc cagaccactg agaaaattag tccgaattgg     120
gaatctggca ttaatgttga cttggcaatt tccacacggc aatatcatct acaacagctt     180
ttctaccgct atggagaaaa taattctttg tcagttgaag ggttcagaaa attacttcaa     240
aatataggca tagataagat taaaagaatc catatacacc atgaccacga ccatcactca     300
gaccacgagc atcactcaga ccatgagcgt cactcagacc atgagcatca ctcagaccac     360
gagcatcact ctgaccatga tcatcactct caccataatc atgctgcttc tggtaaaaat     420
aagcgaaaag ctctttgccc agaccatgac tcagatagtt caggtaaaga tcctagaaac     480
agccagggga aaggagctca ccgaccagaa catgccagtg gtagaaggaa tgtcaaggac     540
agtgttagtg ctagtgaagt gacctcaact gtgtacaaca ctgtctctga aggaactcac     600
tttctagaga caatagagac tccaagacct ggaaaactct cccccaaaga tgtaagcagc     660
tccactccac ccagtgtcac atcaaagagc cgggtgagcc ggctggctgg taggaaaaca     720
aatgaatctg tgagtgagcc ccgaaaaggc tttatgtatt ccagaaacac aaatgaaaat     780
cctcaggagt gtttcaatgc atcaaagcta ctgacatctc atggcatggg catccaggtt     840
ccgctgaatg caacagagtt caactatctc tgtccagcca tcatcaacca aattgatgct     900
agatcttgtc tgattcatac aagtgaaaag aaggctgaaa tccctccaaa gacctattca     960
ttacaaatag cctgggttgg tggttttata gccatttcca tcatcagttt cctgtctctg    1020
ctggggggtta tcttagtgcc tctcatgaat cgggtgtttt tcaaatttct cctgagtttc    1080
cttgtggcac tggccgttgg gactttgagt ggtgatgctt ttttacacct tcttccacat    1140
tctcatgcaa gtcaccacca tagtcatagc catgaagaac cagcaatgga aatgaaaaga    1200
ggaccacttt tcagtcatct gtcttctcaa aacatagaag aaagtgccta ttttgattcc    1260
acgtggaagg tctaacagc tctaggaggc ctgtatttca tgtttcttgt tgaacatgtc    1320
ctcacattga tcaaacaatt taaagataag aagaaaaaga atcagaagaa acctgaaaat    1380
gatgatgatg tggagattaa gaagcagttg tccaagtatg aatctcaact ttcaacaaat    1440
gaggagaaag tagatacaga tgatcgaact gaaggctatt tacgagcaga ctcacaagag    1500
ccctccccact ttgattctca gcagcctgca gtcttggaag aagaagaggt catgatagct    1560
catgctcatc cacaggaagt ctacaatgaa tatgtaccca gagggtgcaa gaataaatgc    1620
cattcacatt tccacgatac actcggccag tcagacgatc tcattcacca ccatcatgac    1680
taccatcata ttctccatca tcaccaccac caaaaccacc atcctcacag tcacagccag    1740
cgctactctc gggaggagct gaaagatgcc ggcgtcgcca ctttggcctg gatggtgata    1800
atgggtgatg gcctgcacaa tttcagcgat ggcctagcaa ttggtgctgc ttttactgaa    1860
ggcttatcaa gtggtttaag tacttctgtt gctgtgttct gtgctgcgtt gcctgctgca    1920
ttaggtgact ttgctgttct actaaaggct ggcatgaccg ttaagcaggc tgtcctttat    1980
aatgcattgt cagccatgct ggcgtatctt ggaatggcaa caggaatttt cattggtcat    2040
tatgctgaaa atgtttctat gtggatattt gcacttactg ctggcttatt catgtatgtt    2100
gctctggttg atatggtacc tgaaatgctg cacaatgatg ctagtgacca tggatgtagc    2160
cgctgggggt atttcttttt acagaatgct gggatgcttt tgggttttgg aattatgtta    2220
cttatttcca tatttgaaca taaaatcgtg tttcgtataa atttc                    2265
```

<210> SEQ ID NO 14
<211> LENGTH: 755
<212> TYPE: PRT
<213> ORGANISM: Artificial Sequence
<220> FEATURE:
<223> OTHER INFORMATION: BCR4 mutant protein sequence

<400> SEQUENCE: 14

```
Met Ala Arg Lys Leu Ser Val Ile Leu Ile Leu Thr Phe Ala Leu Ser
1               5                   10                  15

Val Thr Asn Pro Leu His Glu Leu Lys Ala Ala Ala Phe Pro Gln Thr
            20                  25                  30

Thr Glu Lys Ile Ser Pro Asn Trp Glu Ser Gly Ile Asn Val Asp Leu
        35                  40                  45

Ala Ile Ser Thr Arg Gln Tyr His Leu Gln Gln Leu Phe Tyr Arg Tyr
    50                  55                  60

Gly Glu Asn Asn Ser Leu Ser Val Glu Gly Phe Arg Lys Leu Leu Gln
65                  70                  75                  80

Asn Ile Gly Ile Asp Lys Ile Lys Arg Ile His Ile His His Asp His
                85                  90                  95

Asp His His Ser Asp His Glu His His Ser Asp His Glu Arg His Ser
            100                 105                 110

Asp His Glu His His Ser Asp His Glu His His Ser Asp His Asp His
        115                 120                 125

His Ser His His Asn His Ala Ala Ser Gly Lys Asn Lys Arg Lys Ala
    130                 135                 140

Leu Cys Pro Asp His Asp Ser Asp Ser Ser Gly Lys Asp Pro Arg Asn
145                 150                 155                 160

Ser Gln Gly Lys Gly Ala His Arg Pro Glu His Ala Ser Gly Arg Arg
                165                 170                 175

Asn Val Lys Asp Ser Val Ser Ala Ser Glu Val Thr Ser Thr Val Tyr
            180                 185                 190

Asn Thr Val Ser Glu Gly Thr His Phe Leu Glu Thr Ile Glu Thr Pro
        195                 200                 205

Arg Pro Gly Lys Leu Phe Pro Lys Asp Val Ser Ser Thr Pro Pro
    210                 215                 220

Ser Val Thr Ser Lys Ser Arg Val Ser Arg Leu Ala Gly Arg Lys Thr
225                 230                 235                 240

Asn Glu Ser Val Ser Glu Pro Arg Lys Gly Phe Met Tyr Ser Arg Asn
                245                 250                 255

Thr Asn Glu Asn Pro Gln Glu Cys Phe Asn Ala Ser Lys Leu Leu Thr
            260                 265                 270

Ser His Gly Met Gly Ile Gln Val Pro Leu Asn Ala Thr Glu Phe Asn
        275                 280                 285

Tyr Leu Cys Pro Ala Ile Ile Asn Gln Ile Asp Ala Arg Ser Cys Leu
    290                 295                 300

Ile His Thr Ser Glu Lys Lys Ala Glu Ile Pro Pro Lys Thr Tyr Ser
305                 310                 315                 320

Leu Gln Ile Ala Trp Val Gly Gly Phe Ile Ala Ile Ser Ile Ile Ser
                325                 330                 335

Phe Leu Ser Leu Leu Gly Val Ile Leu Val Pro Leu Met Asn Arg Val
            340                 345                 350

Phe Phe Lys Phe Leu Leu Ser Phe Leu Val Ala Leu Ala Val Gly Thr
        355                 360                 365
```

```
Leu Ser Gly Asp Ala Phe Leu His Leu Pro His Ser His Ala Ser
        370                 375                 380

His His His Ser His Ser His Glu Glu Pro Ala Met Glu Met Lys Arg
385                 390                 395                 400

Gly Pro Leu Phe Ser His Leu Ser Ser Gln Asn Ile Glu Glu Ser Ala
                405                 410                 415

Tyr Phe Asp Ser Thr Trp Lys Gly Leu Thr Ala Leu Gly Gly Leu Tyr
            420                 425                 430

Phe Met Phe Leu Val Glu His Val Leu Thr Leu Ile Lys Gln Phe Lys
        435                 440                 445

Asp Lys Lys Lys Asn Gln Lys Lys Pro Glu Asn Asp Asp Val
450                 455                 460

Glu Ile Lys Lys Gln Leu Ser Lys Tyr Glu Ser Gln Leu Ser Thr Asn
465                 470                 475                 480

Glu Glu Lys Val Asp Thr Asp Arg Thr Glu Gly Tyr Leu Arg Ala
                485                 490                 495

Asp Ser Gln Glu Pro Ser His Phe Asp Ser Gln Gln Pro Ala Val Leu
                500                 505                 510

Glu Glu Glu Val Met Ile Ala His Ala His Pro Gln Glu Val Tyr
            515                 520                 525

Asn Glu Tyr Val Pro Arg Gly Cys Lys Asn Lys Cys His Ser His Phe
530                 535                 540

His Asp Thr Leu Gly Gln Ser Asp Asp Leu Ile His His His His Asp
545                 550                 555                 560

Tyr His His Ile Leu His His His His Gln Asn His Pro His
                565                 570                 575

Ser His Ser Gln Arg Tyr Ser Arg Glu Glu Leu Lys Asp Ala Gly Val
                580                 585                 590

Ala Thr Leu Ala Trp Met Val Ile Met Gly Asp Gly Leu His Asn Phe
            595                 600                 605

Ser Asp Gly Leu Ala Ile Gly Ala Ala Phe Thr Glu Gly Leu Ser Ser
        610                 615                 620

Gly Leu Ser Thr Ser Val Ala Val Phe Cys Ala Ala Leu Pro Ala Ala
625                 630                 635                 640

Leu Gly Asp Phe Ala Val Leu Leu Lys Ala Gly Met Thr Val Lys Gln
                645                 650                 655

Ala Val Leu Tyr Asn Ala Leu Ser Ala Met Leu Ala Tyr Leu Gly Met
                660                 665                 670

Ala Thr Gly Ile Phe Ile Gly His Tyr Ala Glu Asn Val Ser Met Trp
            675                 680                 685

Ile Phe Ala Leu Thr Ala Gly Leu Phe Met Tyr Val Ala Leu Val Asp
        690                 695                 700

Met Val Pro Glu Met Leu His Asn Asp Ala Ser Asp His Gly Cys Ser
705                 710                 715                 720

Arg Trp Gly Tyr Phe Leu Gln Asn Ala Gly Met Leu Leu Gly Phe
                725                 730                 735

Gly Ile Met Leu Leu Ile Ser Ile Phe Glu His Lys Ile Val Phe Arg
                740                 745                 750

Ile Asn Phe
        755

<210> SEQ ID NO 15
<211> LENGTH: 44
<212> TYPE: DNA
<213> ORGANISM: Artificial Sequence
```

-continued

```
<220> FEATURE:
<223> OTHER INFORMATION: Oligonucleotide 5' primer for generating mutant
      BCR4

<400> SEQUENCE: 15
ctttaattaa caccgccacc atggcgagga agttatctgt aatc                         44

<210> SEQ ID NO 16
<211> LENGTH: 41
<212> TYPE: DNA
<213> ORGANISM: Artificial Sequence
<220> FEATURE:
<223> OTHER INFORMATION: Oligonucleotide 5' primer for generating mutant
      BCR4

<400> SEQUENCE: 16
taatgcagca ggcaacgcag cacagaacac agcaacagaa g                            41

<210> SEQ ID NO 17
<211> LENGTH: 38
<212> TYPE: DNA
<213> ORGANISM: Artificial Sequence
<220> FEATURE:
<223> OTHER INFORMATION: Oligonucleotide 3' primer for generating BCR4
      mutant

<400> SEQUENCE: 17
tgctgcgttg cctgctgcat taggtgactt tgctgttc                                38

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide 3' primer for generating BCR4
      mutant

<400> SEQUENCE: 18
gtctcgagga aatttatacg aaac                                               24
```